(12) United States Patent
Lloyd et al.

(10) Patent No.: US 7,833,745 B2
(45) Date of Patent: Nov. 16, 2010

(54) DIRECT DETECTION METHOD FOR PRODUCTS OF CELLULAR METABOLISM USING TOF-SIMS

(75) Inventors: Kathryn G. Lloyd, Wilmington, DE (US); Daniel P. O'Keefe, Ridley Park, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 296 days.

(21) Appl. No.: 10/937,223

(22) Filed: Sep. 8, 2004

(65) Prior Publication Data
US 2006/0188868 A1 Aug. 24, 2006

Related U.S. Application Data

(60) Provisional application No. 60/502,151, filed on Sep. 11, 2003.

(51) Int. Cl.
*H01J 17/26* (2006.01)
*C12Q 1/02* (2006.01)

(52) U.S. Cl. ......................................... 435/29; 313/564
(58) Field of Classification Search ........................ None
See application file for complete search history.

(56) References Cited

U.S. PATENT DOCUMENTS

| 5,914,245 | A | 6/1999 | Bylina et al. |
| 6,472,163 | B1 | 10/2002 | Coleman et al. |
| 2003/0116707 | A1 | 6/2003 | Brown et al. |
| 2004/0132080 | A1 | 7/2004 | Kawaguchi et al. |

FOREIGN PATENT DOCUMENTS

WO WO 00/48004 A1 8/2000

OTHER PUBLICATIONS

Verran et al. J of Food Protection 2001;64(9):1377-1387.*
Cheran et al. Analyst 2003;128:126-129.*
Colliver et al. "Atomic and molecular imaging at the single-cell level with TOF-SIMS", Anal. Chem. 1997, 69:2225-2231.*
Ben Cliff et al., Probing cell chemistry with time-of-light secondary ion mass spectrometry: development and exploitation of instrumentation for studies of frozen-hydrated biological material, Rapid Communications in Mass Spectrometry, vol. 17:2163-2167, 2003.
Roger Michel et al., Selective Molecular Assembly Patterning: A New Approach to Micro- and Nanochemical Patterning of Surfaces for Biological Applications, Langmuir, vol. 18:3281-3287, 2002.
Thomas L. Colliver et al., Atomic and Molecular Imaging at the Single-Cell Level with TOF-SIMS, Anal. Chem., vol. 69:2225-2231, 1997.
Peter Sjovall et al., Imaging of Membrane Lipids in Single Cells by Imprint-Imaging Time-of-Flight Secondary Ion Mass Spectrometry, Anal. Chem., vol. 75:3429-3434, 2003.
Michaeleen L. Pacholski et al., Static Time-of-flight Secondary Ion Mass Spectrometry Imaging of Freeze-fractured, Frozen-hydrated Biological Membranes, Rapid Communications in Mass Spectrometry, vol. 12:1232-1235, 1998.
Robert M. Braun et al., Spatially Resolved Detection of Attomole Quantities of Organic Molecules Localized in Picoliter VialsUsing Time-of-Flight Secondary Ion Mass Spectrometry, Anal. Chem., vol. 71:3318-3324, 1999.
Donald M. Cannon, Jr. et al., Molecule Specific Imaging of Freeze-Fractured. Frozen-Hydrated Model Membrane Systems Using Mass Spectrometry, J. Am. Chem. Soc., vol. 122:603-610, 2000.
Werner Edgar Glabgen et al., Metabolism of the Herbicide Isoproturon in Wheat and Soybean Cell Suspension Cultures, Pesticide Biochemistry and Physiology, vol. 63:97-113, 1999.
Bonnie J. Tyler et al., Multivariate Statistical Approaches for Interpreting TOF-SIMS Spectra of Bacterial and Fungal Cell Walls, Proceedings of the 12$^{th}$ International Conference on Secondary Ion Mass Spectrometry, Brussels, Belgium, 1999.
H.-U. JABS, Characterization of an Apolipoprotein C-III Mutant by High-Performance Liquid Chromatography and Time-of-Flight Secondary Ion Mass Spectrometry, J. of Chromatography, vol. 414:323-333, 1987.

* cited by examiner

*Primary Examiner*—Jon P. Weber
*Assistant Examiner*—Bin Shen

(57) ABSTRACT

A rapid and efficient method for novel biological substance screening by surface analysis has been developed using Time-of-Flight Secondary Ion Mass Spectrometry (ToF-SIMS). This method relies on the surface screening of an array of micro-organisms grown on porous membranes, which had previously been in contact with a solid growth medium. ToF-SIMS analysis differentiates among organisms producing different substances, either directly as molecular product, or indirectly through the use of multivariate statistical data reduction techniques. This method has many advantages over traditional microbial screening methods, which require sample preparation and time for assay development.

23 Claims, 14 Drawing Sheets

Field of view: 20000.0 x 20000.0 µm²

M:Chlorine
tc:7568721

M:CNO+phosphate
tc:1035697

M:Br+[485-489]
tc:208332

SEQUENCE LISTING

```
<160> NUMBER OF SEQ ID NOS: 1

<210> SEQ ID NO 1
<211> LENGTH: 10328
<212> TYPE: DNA
<213> ORGANISM: artificial sequence
<220> FEATURE:
<223> OTHER INFORMATION: synthetic DNA fragment incuding genes for
      production of eicosapentenoic acid

<400> SEQUENCE: 1
tatcacatca cgctctcatc aagaatactt cttgagaacc gtggagaccg gggttcgatt      60
ccccgtatcg gagtgtttat tttttgctca accatacccT ggggtgtgtt ctgtggagca     120
ttctcacttt tggtaaacga cattgcttca agtgcagcgg aatcaaaaag tataaagtgg     180
gcagcgagta tacctgtaca gactgtaggc gataactcaa tccaattacc ccccacaaca     240
tgactggcca aactgatctc aagactttat tgaaatcagc aacaccgatt ctcaatgaag     300
gcacatactt cttctgcaac attcacttga cgcctaaagt tggtgagaaa tggaccgaca     360
agacatattc tgctatccac ggactgttgc ctgtgtcggt ggctacaata cgtgagtcag     420
aagggctgac ggtggtggtt cgtacgttgt gtggaattgt gagcggataa caatttcaca     480
caggaaacag ctatgaccat gattacgcca agctcgaaat taaccctcac taaagggaac     540
aaaagctgga gctccaccgc ggacacaata tctggtcaaa tttcagtttc gttacataaa     600
tcgttatgtc aaaggagtgt gggaggttaa gagaattatc accggcaaac tatctgttaa     660
ttgctaggta cctctagacg tccacccggg tcgcttggcg gccgaagagg ccggaatctc     720
```

```
gggccgcggt ggcggccgct tactgcaact tccttgcctt ctccttggca gcgtcggcct      780
tggcctgctt ggccaacttg gcgttctttc tgtaaaagtt gtagaagaga ccgagcatgg      840
tccacatgta gaaccaaagc agagccgtga tgaagaaggg gtatccgggg cggccaagga      900
ccttcatggc gtacatgtcc caggaagact ggaccgacat catgcagaac tgtgtcatct      960
gcgagcgcgt gatgtagaac ttgatgaacg cacctgcctt gaagcccaag gccgacaaga     1020
agtagtagcc gtacatgatc acatggatga acgagttcaa cgcagcagag aagtaggctt     1080
caccgttggg tgcaacaaag gtgaccaacc accagatggt gaagatggag ctgtggtggt     1140
aaacgtgcaa gaaggagatc tggcggttgt tcttcttgag gaccatgatc atggtgtcga     1200
caaactccat gatcttggag aagtagaaga gccagatcat cttggccata ggaagaccct     1260
tgaaggtatg atcagcagcg ttctcaaaca gtccatagtt ggcctgataa gcctcgtaca     1320
ggatcccacc gcacatgtag gcgctgatcg agaccagaca aaagttgtgc aggagcgaaa     1380
acgtcttgac ctcgaaccgc tcaaagttct tcatgatctg catgcccaca agaccgtga     1440 ccaaataagc gagcacgatc aacagcacgt ggaacgggtt catcaacggc agctcacggg     1500
ccaaaggcga ctccaccgcg accaggaacc cacgcgtgtg atggacaatc gtggggatgt     1560
acttctcggc ctgggccacc agcgcggcct cgagaggatc gacatagggc gcggcccgga     1620
caccgatagc ggtggcaagg tccataaaca gatcttgcgg catctttgat gggaggaatg     1680
gcgcaatcga ctccatgcgg ccgctctaga actagtggat cctttgaatg attcttatac     1740
tcagaaggaa atgcttaacg atttcgggtg tgagttgaca aggagagaga gaaaagaaga     1800
ggaaaggtaa ttcggggacg gtggtctttt atacccttgg ctaaagtccc aaccacaaag     1860
caaaaaaatt ttcagtagtc tattttgcgt ccggcatggg ttacccggat ggccagacaa     1920
agaaactagt acaaagtctg aacaagcgta gattccagac tgcagtaccc tacgccctta     1980
acggcaagtg tgggaaccgg gggaggtttg atatgtgggg tgaaggggc tctcgccggg      2040 gttgggcccg ctactgggtc aatttggggt caattggggc aattggggct gttttttggg     2100
acacaaatac gccgccaacc cggtctctcc tgaagcttgt gagcggataa caatttcaca     2160
caggaaacag ctatgaccat gattacgcca agctcgaaat taaccctcac taaagggaac     2220
aaaagctgga gctccaccgc ggacacaata tctggtcaaa tttcagtttc gttacataaa     2280
tcgttatgtc aaaggagtgt gggaggttaa gagaattatc accggcaaac tatctgttaa     2340
ttgctaggta cctctagacg tccacccggg tcgcttggcg gccgaagagg ccggaatctc     2400
gggccgcggt ggcggccgcc tactcttcct tgggacggag tccaagaaca cgcaagtgct     2460
ccaaatgtga agcaaatgct tgccaaaacg tatccttgac aaggtatgga accttgtact     2520
cgctgcaggt gttcttgatg atggccagaa tatcgggata atggtgctgc gacacgttgg     2580
ggaacagatg gtgcacagcc tggtagttca agctgccagt gatgctggtc cagaggtgcg     2640
aatcgtgtgc gtaatcctgc gtagtctcga cctgcatagc tgcccagtcc ttttggatga     2700
tcccgttctc gtcaggcaac ggccactgaa cttcctcaac aacgtggttc gcctggaagg     2760
tcagcgccag ccagtaagac gacaccatgt ccgcgaccgt gaacaagagc agcaccttgc     2820
ccaggggcag atactgcagg ggaacaatca ggcgatacca gacaaagaaa gccttgccgc     2880
cccagaacat cacagtgtgc catgtcgaga tgggattgac acgaatagcg tcattggtct     2940
tgacaaagta caaatgttg atgtcctgaa tgcgcacctt gaacgccagc agtccgtaca     3000
ggaaaggaac aaacatgtgc tggttgatgt ggttgacaaa ccacttttgg ttgggcttga     3060
tacgacgaac atcgggctca gacgtcgaca cgtcgggatc tgctccagca atgttggtgt     3120
```

```
aggggtgatg gccgagcata tgttggtaca tccacaccag gtacgatgct ccgttgaaaa   3180
agtcgtgcgt ggctcccaga atcttccaga cagtggggtt gtgggtcact gaaaagtgag   3240
acgcatcatg aagagggttg agtccgactt gtgcgcacgc aaatcccatg atgattgcaa   3300
acaccacctg aagccatgtg cgttcgacaa cgaaaggcac aaagagctgc gcgtagtagg   3360
aagcgatcaa ggatccaaag ataagagcgt atcgtcccca gatctctggt ctattcttgg   3420
gatcaatgtt ccgatccgta agtagccct cgactctcgt cttgatggtt ttgtggaaca   3480
ccgttggctc cgggaagatg ggcagctcat tcgagaccag tgtaccgaca tagtacttct   3540
tcataatggc atctgcagcc ccaaacgcgt gatacatctc aaagaccgga gtaacatctc   3600
ggccagctcc gagcaggaga gtgtccactc caccaggatg gcggctcaag aactttgtga   3660
catcgtacac cctgccgcgg atggccaaga gtaggtcgtc cttggtgtta tgggccgcca   3720
gctcttccca ggtgaaggtt tttccttggt ccgttcccat ggtgaatgat tcttatactc   3780
agaaggaaat gcttaacgat tcgggtgtg agttgacaag gagagagaga aagaagagg    3840 aaggtaatt cggggacggt ggtctttat acccttggct aaagtcccaa ccacaaagca    3900
aaaaaatttt cagtagtcta ttttgcgtcc ggcatgggtt acccggatgg ccagacaaag   3960
aaactagtac aaagtctgaa caagcgtaga ttccagactg cagtacccta cgcccttaac   4020
ggcaagtgtg ggaaccgggg gaggtttgat atgtggggtg aaggggggctc tcgccggggt   4080 tgggcccgct actgggtcaa tttggggtca attgggggcaa ttggggctgt ttttgggac    4140 acaaatacgc cgccaacccg gtctctcctg aattctgcag atgggctgca ggaattccgt   4200
cgtcgcctga gtcgacatca tttatttacc agttggccac aaaccccttga cgatctcgta   4260 tgtcccctcc gacatactcc cggccggctg gggtacgttc gatagcgcta tcggcatcga   4320
caaggtttgg gtccctagcc gataccgcac tacctgagtc acaatcttcg gaggtttagt   4380
cttccacata gcacgggcaa aagtgcgtat atatacaaga gcgtttgcca gccacagatt   4440
ttcactccac acaccacatc acacatacaa ccacacacat ccacaatgga acccgaaact   4500
aagaagacca agactgactc caagaagatt gttcttctcg gcggcgactt ctgtggcccc   4560
gaggtgattg ccgaggccgt caaggtgctc aagtctgttg ctgaggcctc cggcaccgag   4620
tttgtgtttg aggaccgact cattggagga gctgccattg agaaggaggg cgagcccatc   4680
accgacgcta ctctcgacat ctgccgaaag gctgactcta ttatgctcgg tgctgtcgga   4740
ggcgctgcca acaccgtatg gaccactccc gacggacgaa ccgacgtgcg acccgagcag   4800
ggtctcctca agctgcgaaa ggacctgaac ctgtacgcca acctgcgacc ctgccagctg   4860
ctgtcgccca agctcgccga tctctccccc atccgaaacg ttgagggcac cgacttcatc   4920
attgtccgag agctcgtcgg aggtatctac tttggagagc gaaaggagga tgacggatct   4980
ggcgtcgctt ccgacaccga gacctactcc gttcctgagg ttgagcgaat tgcccgaatg   5040
gccgccttcc tggcccttca gcacaacccc cctcttcccg tgtggtctct tgacaaggcc   5100
aacgtgctgg cctcctctcg actttggcga aagactgtca ctcgagtcct caaggacgaa   5160
ttcccccagc tcgagctcaa ccaccagctg atcgactcgg ccgccatgat cctcatcaag   5220
cagccctcca agatgaatgg tatcatcatc accaccaaca tgtttggcga tatcatctcc   5280
gacgaggcct ccgtcatccc cggttctctg ggtctgctgc cctccgcctc tctggcttct   5340
ctgcccgaca ccaacgaggc gttcggtctg tacgagccct gtcacggatc tgcccccgat   5400
ctcggcaagc agaaggtcaa ccccattgcc accattctgt ctgccgccat gatgctcaag   5460
```

```
ttctctctta acatgaagcc cgccggtgac gctgttgagg ctgccgtcaa ggagtccgtc    5520
gaggctggta tcactaccgc cgatatcgga ggctcttcct ccacctccga ggtcggagac    5580
ttgttgccaa caaggtcaag gagctgctca agaaggagta agtcgtttct acgacgcatt    5640
gatggaagga gcaaactgac gcgcctgcgg gttggtctac cggcagggtc cgctagtgta    5700
taagactcta taaaaggggc cctgccctgc taatgaaatg atgatttata atttaccggt    5760
gtagcaacct tgactagaag aagcagattg ggtgtgtttg tagtggagga cagtggtacg    5820
ttttggaaac agtcttcttg aaagtgtctt gtctacagta tattcactca taacctcaat    5880
agccaagggt gtagtcggtt tattaaagga agggagttgt ggctgatgtg gatagatatc    5940
tttaagctgg cgactgcacc caacgagtgt ggtggtagct tgttactgta tattcggtaa    6000
gatatatttt gtggggtttt agtggtgttt aaacgacgga attcctgcag cccatctgca    6060
gaattcagga gagaccgggt tggcggcgta tttgtgtccc aaaaaacagc cccaattgcc    6120
ccaattgacc ccaaattgac ccagtagcgg gcccaacccc ggcgagagcc cccttcaccc    6180
cacatatcaa acctcccccg gttcccacac ttgccgttaa gggcgtaggg tactgcagtc    6240
tggaatctac gcttgttcag actttgtact agtttctttg tctggccatc cgggtaaccc    6300
atgccggacg caaaatagac tactgaaaat ttttttgctt tgtggttggg actttagcca    6360
agggtataaa agaccaccgt ccccgaatta cctttcctct tcttttctct ctctccttgt    6420
caactcacac ccgaaatcgt taagcatttc cttctgagta taagaatcat tcaccatggc    6480
tgaggataag accaaggtcg agttccctac cctgactgag ctgaagcact ctatccctaa    6540
cgcttgcttt gagtccaacc tcggactctc gctctactac actgcccgag cgatcttcaa    6600
cgcatctgcc tctgctgctc tgctctacgc tgcccgatct actcccttca ttgccgataa    6660
cgttctgctc cacgctctgg tttgcgccac ctacatctac gtgcagggtg tcatcttctg    6720
gggtttcttt accgtcggtc acgactgtgg tcactctgcc ttctcccgat accactccgt    6780
caacttcatc attggctgca tcatgcactc tgccattctg actcccttcg agtcctggcg    6840
agtgaccccac cgacaccatc acaagaacac tggcaacatt gataaggacg agatcttcta    6900
ccctcatcgg tccgtcaagg acctccagga cgtgcgacaa tgggtctaca ccctcggagg    6960
tgcttggttt gtctacctga aggtcggata tgctcctcga accatgtccc actttgaccc    7020
ctgggaccct ctcctgcttc gacgagcctc cgctgtcatc gtgtccctcg gagtctgggc    7080
tgccttcttc gctgcctacg cctacctcac atactcgctc ggctttgccg tcatgggcct    7140
ctactactat gctcctctct ttgtctttgc ttcgttcctc gtcattacta ccttcttgca    7200
tcacaacgac gaagctactc cctggtacgg tgactcggag tggacctacg tcaagggcaa    7260
cctgagctcc gtcgaccgat cgtacggagc tttcgtggac aacctgtctc accacattgg    7320
cacccaccag gtccatcact tgttccctat cattccccac tacaagctca acgaagccac    7380
caagcacttt gctgccgctt accctcacct cgtgagacgt aacgacgagc ccatcattac    7440
tgccttcttc aagaccgctc acctctttgt caactacgga gctgtgcccg agactgctca    7500
gattttcacc ctcaaagagt ctgccgctgc agccaaggcc aagagcgacc accaccatca    7560
ccaccattaa gcggccgcca ccgcggcccg agattccggc ctcttcggcc gccaagcgac    7620
ccgggtggac gtctagaggt acctagcaat taacagatag tttgccggtg ataattctct    7680
taacctccca cactcctttg acataacgat ttatgtaacg aaactgaaat ttgaccagat    7740
attgtgtccg cggtggagct ccagcttttg ttccctttag tgagggttaa tttcgagctt    7800
ggcgtaatcg atgcagaatt caggagagac cgggttggcg gcgtatttgt gtcccaaaaa    7860
```

```
acagccccaa ttgccccaat tgaccccaaa ttgacccagt agcgggccca accccggcga   7920
gagccccctt caccccacat atcaaacctc cccggttcc cacacttgcc gttaagggcg    7980
tagggtactg cagtctggaa tctacgcttg ttcagacttt gtactagttt ctttgtctgg   8040
ccatccgggt aacccatgcc ggacgcaaaa tagactactg aaaattttt tgctttgtgg    8100 ttgggacttt agccaagggt ataaaagacc accgtccccg aattacctt cctcttcttt    8160 tctctctctc cttgtcaact cacacccgaa atcgttaagc atttccttct gagtataaga   8220
atcattcacc atggctgctg ctcccagtgt gaggacgttt actcgggccg aggttttgaa   8280
tgccgaggct ctgaatgagg gcaagaagga tgccgaggca cccttcttga tgatcatcga   8340
caacaaggtg tacgatgtcc gcgagttcgt ccctgatcat cccggtggaa gtgtgattct   8400
cacgcacgtt ggcaaggacg gcactgacgt cttgacact tttcaccccg aggctgcttg    8460
ggagactctt gccaactttt acgttggtga tattgacgag agcgaccgcg atatcaagaa   8520
tgatgacttt gcggccgagg tccgcaagct gcgtaccttg ttccagtctc ttggttacta   8580
cgattcttcc aaggcatact acgccttcaa ggtctcgttc aacctctgca tctgggttt    8640 gtcgacggtc attgtggcca agtggggcca gacctcgacc ctcgccaacg tgctctcggc   8700
tgcgcttttg ggtctgttct ggcagcagtg cggatggttg gctcacgact ttttgcatca   8760
ccaggtcttc caggaccgtt tctggggtga tcttttcggc gccttcttgg gaggtgtctg   8820
ccagggcttc tcgtcctcgt ggtggaagga caagcacaac actcaccacg ccgcccccaa   8880
cgtccacggc gaggatcccg acattgacac ccaccctctg ttgacctgga gtgagcatgc   8940
gttggagatg ttctcggatg tcccagatga ggagctgacc cgcatgtggt cgcgtttcat   9000
ggtcctgaac cagacctggt tttacttccc cattctctcg tttgcccgtc tctcctggtg   9060
cctccagtcc attctctttg tgctgcctaa cggtcaggcc cacaagccct cgggcgcgcg   9120
tgtgcccatc tcgttggtcg agcagctgtc gcttgcgatg cactggacct ggtacctcgc   9180
caccatgttc ctgttcatca aggatcccgt caacatgctg gtgtacttt tggtgtcgca    9240 ggcggtgtgc ggaaacttgt tggccatcgt gttctcgctc aaccacaacg gtatgcctgt   9300
gatctcgaag gaggaggcgg tcgatatgga tttcttcacg aagcagatca tcacgggtcg   9360
tgatgtccac ccgggtctat ttgccaactg gttcacgggt ggattgaact atcagatcga   9420
gcaccacttg ttcccttcga tgcctcgcca caacttttca aagatccagc ctgctgtcga   9480
gaccctgtgc aaaaagtaca atgtccgata ccacaccacc ggtatgatcg agggaactgc   9540
agaggtcttt agccgtctga cgaggtctc caaggctacc tccaagatgg gtaaggcgca    9600
gtaagcggcc gccaccgcgg cccgagattc cggcctcttc ggccgccaag cgacccgggt   9660
ggacgtctag aggtacctag caattaacag atagtttgcc ggtgataatt ctcttaacct   9720
cccacactcc tttgacataa cgatttatgt aacgaaactg aaatttgacc agatattgtg   9780
tccgcggtgg agctccagct tttgttccct ttagtgaggg ttaattaatt cgatatcata   9840
attgtcggcc gaggtctgta cggccagaac cgagatccta ttgaggaggc caagcgatac   9900
cagaaggctg gctgggaggc ttaccagaag attaactgtt agaggttaga ctatggatat   9960
gtcatttaac tgtgtatata gagagcgtgc aagtatggag cgcttgttca gcttgtgatga  10020 tggtcagacg acctgtctga tcgagtatgt atgatactgc acaacctgtg tatccgcatg   10080
atctgtccaa tggggcatgt tgttgtgttt ctcgatacgg agatgctggg tacaagtagc   10140
taatacgatt gaactactta tacttatatg aggcttgaag aaagctgact tgtgtatgac   10200
```

-continued

```
ttattctcaa ctacatcccc agtcacaata ccaccactgc actaccacta caccaaaacc    10260
atgatcaaac cacccatgga cttcctggag gcagaagaac ttgttatgga aaagctcaag    10320
agagagaa                                                             10328
```

DIRECT DETECTION METHOD FOR PRODUCTS OF CELLULAR METABOLISM USING TOF-SIMS

This patent application claims the benefit of U.S. Provisional Patent Application U.S. Ser. No. 60/502151, filed Sep. 11, 2003.

FIELD OF THE INVENTION

This invention is in the field of microbiology. More specifically, this invention pertains to methods for the detection of cellular products by time-of-flight mass spectometry.

BACKGROUND OF THE INVENTION

There are many different techniques currently available to screen biological samples or collections, and mutant or gene-expression libraries for those individuals that have distinguishing or desired characteristics. Most procedures require individual colonies that are grown from the samples, collections or libraries to be picked from Petri dish into microtiter dish format, then incubated for a period of time to allow growth, followed by considerable sample handling and preparation, all of which is prior to the analytical step. When many individuals must be analyzed, these steps are undesirable. Methods of analysis that require less sample preparation have been developed for use in screening large numbers of samples.

An improvement to mass spectrometry sample screening methods allowing high throughput assay of many samples was described in WO 00/48004. This method eliminates the column separation step that is generally required prior to sample injection into the mass spectrometer by purifying components of interest using processes such as adding a volatile buffer, an organic solvent, or an ion exchange resin. In addition, components could be purified by attachment to a solid support. However, this method still requires that prior to the analysis, some purification of component(s) of interest is performed, and the purified sample is then injected into a mass spectrometer.

Elimination of sample component purification in a screening method is described in U.S. Pat. No. 5,914,245. In this method, microcolonies of cells on a base are optically monitored over time for changes in an optically detectable signal. The optically detectable signal arises from contacting the cells with an optical signal substrate, from which the optically detectable signal is produced through an enzymatic reaction. The monitoring of the optically detectable signal over time allows for characterization of the activity of the enzyme produced by the microcolony. In this method the cells may be lysed or permeabilized to expose the optical signal substrate to the cellular contents. Though this method does eliminate sample purification steps prior to analysis, its limitation is that the analysis is based on optical detection, which makes the method applicable only in cases where optical substrates with appropriate absorbance or fluorescence properties are available for the enzyme to be assayed.

In U.S. Pat. No. 6,472,163, the method of U.S. Pat. No. 5,914,245 is improved through the use of different types of microporous membranes, which are easy to handle and have chemical resistance, as the base. Additional improvements include better temperature control, more compact illumination systems, and the use of different indicators for direct and indirect assays or coupled assays. The limitation remains that all assays are monitored by absorbance or fluorescence techniques.

Detection of organic molecules using Time-of-Flight Secondary Ion Mass Spectrometry (ToF-SIMS) in a high-density array sample format is described in Braun et al. (*Anal. Chem.* (1999) 71: 3318-3324). In this process samples are injected into silicon nanovials, which provides for analysis of femtoliter to picoliter sample volumes with compound concentrations of $\times 10^{-2}$ to $1 \times 10^{-4}$ molar allowing detection of attomole to femtomole quantities of molecules. This approach is required when the only means of mapping is via rastering of the primary ion beam, which limits the field of view to less than $1000 \times 1000 \ \mu m^2$. Thus the extremely sensitive capacity of the ToF-SIMS detection was applied in a high throughput miniaturized assay system, however only solutions containing a pure compound were assayed. Thus this assay system, as described, is applicable to simple solutions that require transfer of femtoliters into an array of chambers prior to analysis. Extension to screening of microbial products still requires culturing time and considerable sample handling to transfer large numbers of complex and/or filtered solutions to the array.

The TOF-SIMS assay technique has been used previously in the analysis of many types of biological samples, all of which have required sample preparation procedures prior to placement of the sample in the ToF-SIMS instrument. Types of biological samples that have been analyzed by TOF-SIMS include peptides prepared from purified proteins (Jabs and Assmann; *Journal of Chromatography* (1987) 414(2): 323-333), protein or other cellular components binding to metal surfaces (Michel et al. *Langmuir* (2002) 18(8):3281-3287; Sjoevall et al. *Analytical Chemistry* (2003) 75(14): 3429-3434), microbial cell walls in freeze-dried preparations (Tyler et al, *Proceedings of the International Conference on Secondary Ion Mass Spectrometry,* 12th, (2000) pp 943-946, Editors: Benninghoven, Alfred. Publisher: Elsevier Science B.V., Amsterdam, Neth.), model phospholipid membranes following freeze-fracture (Cannon et al. *Journal of the American Chemical Society* (2000), 122(4): 603-610), freeze-fractured and frozen-hydrated liposomes and red blood cells (Pacholski et al., *Rapid Communications in Mass Spectrometry* (1998), 12(18:1232-1235), freeze-fractured and frozen hydrated paramecium (Colliyer et al., *Analytical Chemistry* (1997), 69(13): 2225-2231), and radioactive isotope labeled compounds in fractionated cells (Glassgen et al., *Pesticide Biochemistry and Physiology* (1999), 63(2): 97-113).

All of the methodologies and biological sample types described above have limitations for screening of large numbers of samples to identify the rare, desired sample due to sample handling and/or detection processes. The problem to be solved, therefore, is to develop a methodology that would permit direct analysis of individual organisms without sample handling and preparation and without restriction to absorbance and fluorescence techniques.

Applicants have solved the stated problem by developing a rapid and efficient method of applying Time-of-Flight Secondary Ion Mass Spectrometry (ToF-SIMS) to the analysis of intact microorganisms. Using this method, biological products of organisms that are intact upon introduction into the ToF-SIMS instrument are screened by surface analysis to allow characterization of the individual organism. The individuals are grown on, or transferred to, the surface of a membrane such that they form an array. Further, the array of intact organisms may be processed in situ and directly introduced into the ToF-SIMS instrument. Use of this method allows rapid screening of arrays of mixed populations of microorganisms such that individuals having different cell contents are identified. Therefore this method provides a substantial advancement over available methods of screening large biological collections to identify individuals of interest.

SUMMARY OF THE INVENTION

The present invention provides a method of using TOF-SIMS to detect differences in biological organisms. In one embodiment the organisms are provided on a vacuum compatible support, for introduction to the ToF-SIMS instrument. In a second embodiment the organisms form an array on the vacuum compatible support and the organisms are intact upon introduction to the TOF-SIMS instrument. In a third embodiment the array of organisms, grown on a primary medium, are contacted with a secondary medium to produce a TOF-SIMS detectable product. In a fourth embodiment the array of organisms is contacted with a substance to produce a ToF-SIMS detectable product. The array of organisms is mapped to correlate the TOF-SIMS data with individuals in the array. The array of organisms may be replicated to provide living samples correlating to the assayed samples.

Accordingly the invention provides a method for identifying a biological organism making a ToF-SIMS detectable product comprising:
 a) providing a colony comprised of biological organisms, on a vacuum compatible support, wherein the biological organisms of the colony produce a product detectable by TOF-SIMS;
 b) performing TOF-SIMS analysis on the colony of (a) to produce data; and
 c) correlating the data of (b) with the colony of (a) whereby biological organism making a ToF-SIMS detectable product is identified.

In an alternate embodiment the invention provides a method for identifying a biological organism making a TOF-SIMS detectable product comprising:
 a) providing a mixed population of biological organisms presented in a two dimensional array on a vacuum compatible support wherein at least one of the organisms produces a product detectable by TOF-SIMS;
 b) performing TOF-SIMS analysis on the array of organisms of (a) to produce data;
 c) mapping said array wherein each organism is supplied with a unique locus on the array;
 d) identifying at least one locus on the array where a ToF-SIMS detectable product is present; and
 e) correlating said data with the unique organism locus of (c) whereby the organism producing a ToF-SIMS detectable product is identified.

Similarly the invention provides a method for identifying a biological organism making a ToF-SIMS detectable product comprising:
 a) providing a mixed population of biological organisms presented in a two dimensional array on a vacuum compatible support wherein at least one of the organisms produces a primary product;
 (b) contacting the array of (a) with a substance under conditions whereby the primary product reacts to produce a ToF-SIMS detectable product;
 c) performing TOF-SIMS analysis on the array of organisms of (a) to produce data;
 d) mapping said array wherein each organism is supplied with a unique locus on the array;
 e) identifying at least one locus on the array where a ToF-SIMS detectable product is present; and
 f) correlating said data with the unique organism locus of (d) whereby the organism producing a ToF-SIMS detectable product is identified.

In another embodiment the invention provides a method for identifying a biological organism making a TOF-SIMS detectable product comprising:
 a) providing a mixed population of biological organisms presented in a two dimensional array on a vacuum compatible support;
 b) transferring the array to a secondary growth medium wherein at least one of the biological organisms incubated on the secondary growth medium produces a product detectable by TOF-SIMS;
 c) performing ToF-SIMS analysis on the array of organisms of (a) to produce TOF-SIMS data;
 d) mapping said array wherein each organism is supplied with a unique locus on the array;
 e) identifying at least one locus on the array where a TOF-SIMS detectable product is present; and
 f) correlating said data with the unique organism locus of (d) whereby the organism producing a ToF-SIMS detectable product is identified.

BRIEF DESCRIPTION OF THE FIGURES AND SEQUENCE DESCRIPTIONS

FIGS. 1A, 1B, 1C, and 1D show the positive (A,B) and negative (C,D) TOF-SIMS spectra acquired from a white X-Gal-fed $E.$ $coli$ colony (A,C) and a blue X-Gal-fed $E.$ $coli$ colony.

Figure 4:
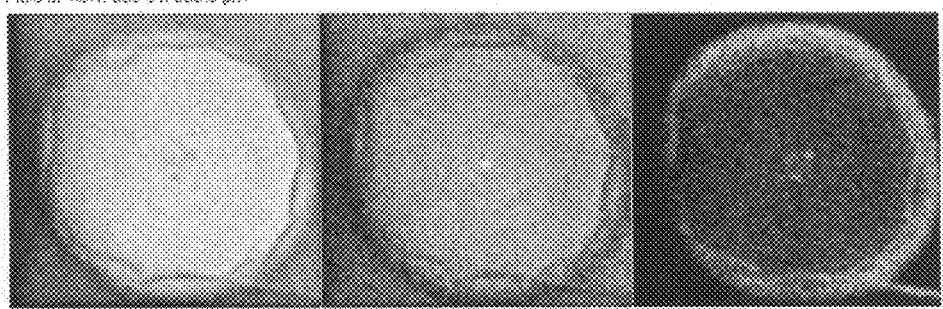
Figure 4:
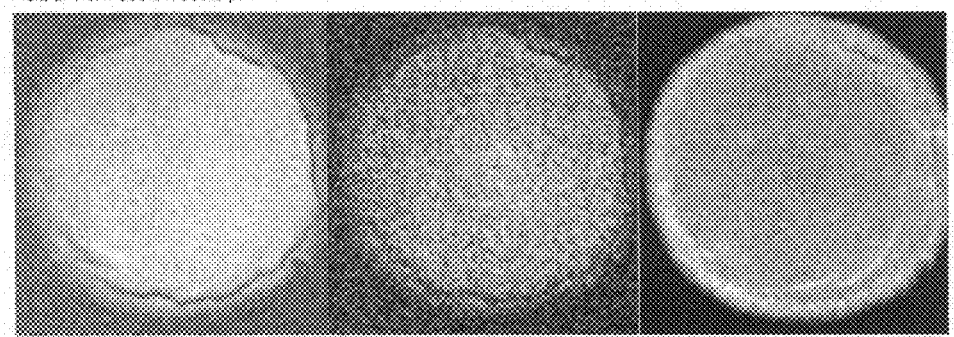

FIGS. 4A and B show TOF-SIMS negative secondary ion maps of an X-Gal fed $E.$ $coli$ colony, where gold $Au_1$ and $Au_3$ ion beams were used.

Figure 5:
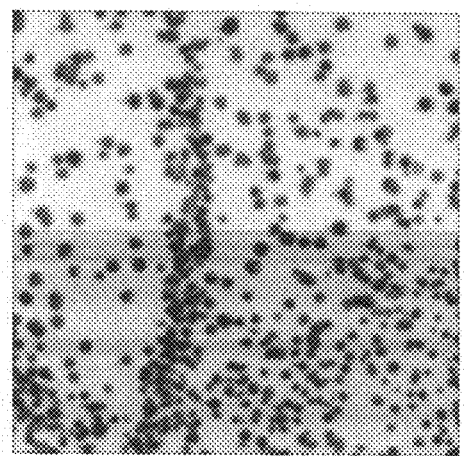
Figure 5:
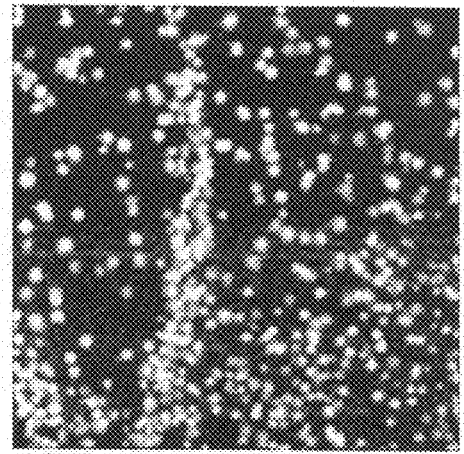
Figure 5:
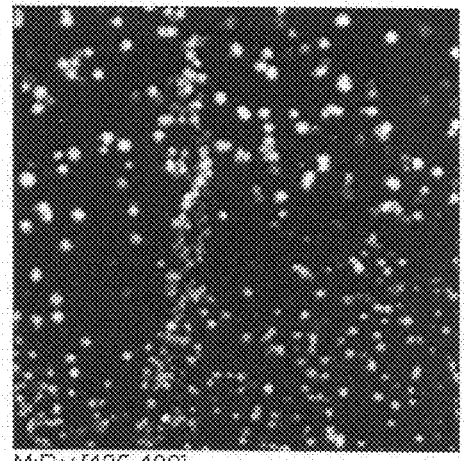

FIGS. 5A, B, and C show spatial distribution maps produced from specific peak intensities from the TOF-SIMS mass spectral data at each pixel of an array of colonies. A: the distribution of Chlorine: B: the distribution of [phosphate+amide/CNO] secondary ions; C: the distribution of Bromine plus indigo molecular secondary ions.

Figure 6:
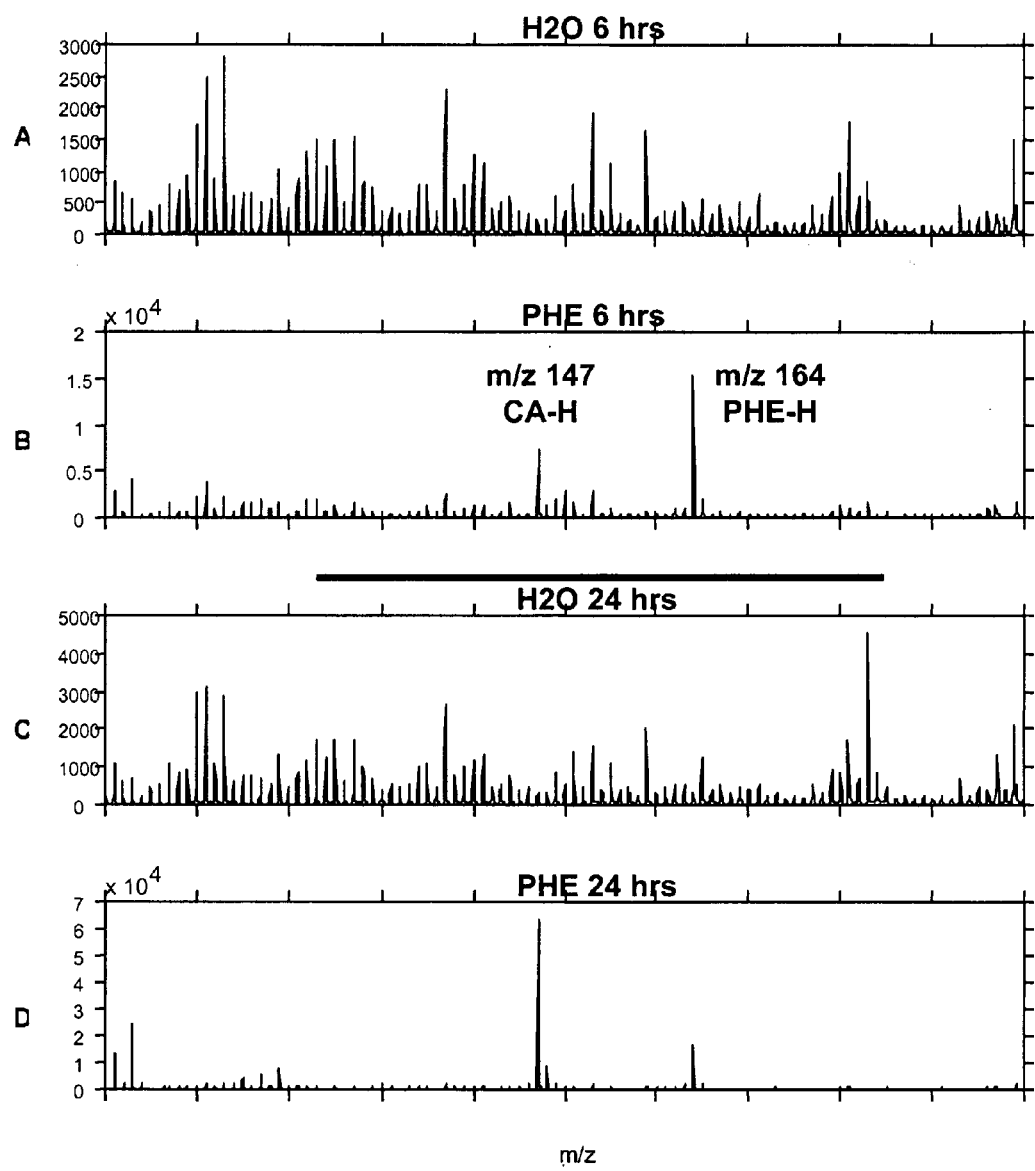

FIG. 6 shows the negative TOF-SIMS data from $E.$ $coli$ fed water (A, C) or phenylananine (B, D) after 6 hours (A, B) or 24 hours (C, D).

FIGS. 7A, B, and C show results of Principal Components Analysis and Multivariate Curve Resolution applied to positive and negative ToF-SIMS data acquired from 11 colonies from a mixture of petal and pET-24d $E.$ $coli$. A: concentrations of Factor 1 and Factor 2 in each colony; B: computed positive TOF-SIMS spectrum associated with Factor 1, Factor 2; C: computed negative TOF-SIMS spectrum associated with Factor 1, Factor 2.

Figure 8:
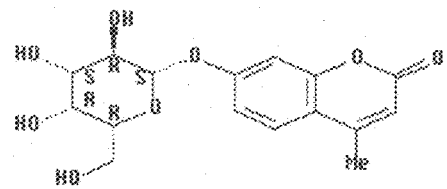
Figure 8:
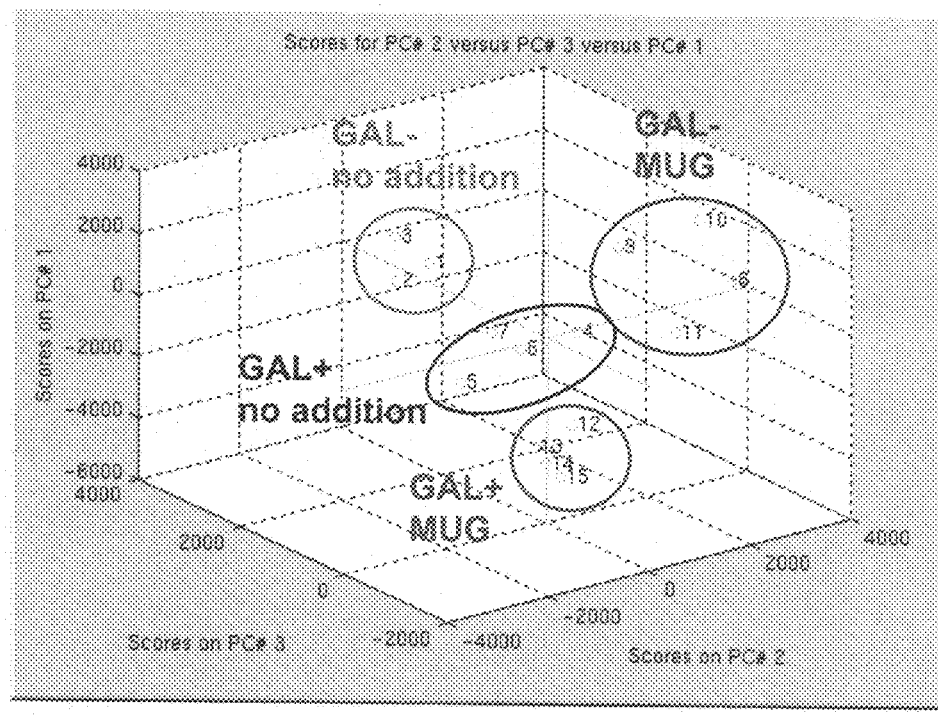

FIG. 8 shows a Principal Components scores plot generated from TOF-SIMS data of $E.$ $coli$ β-galactosidase/MUG samples.

Figure 9:
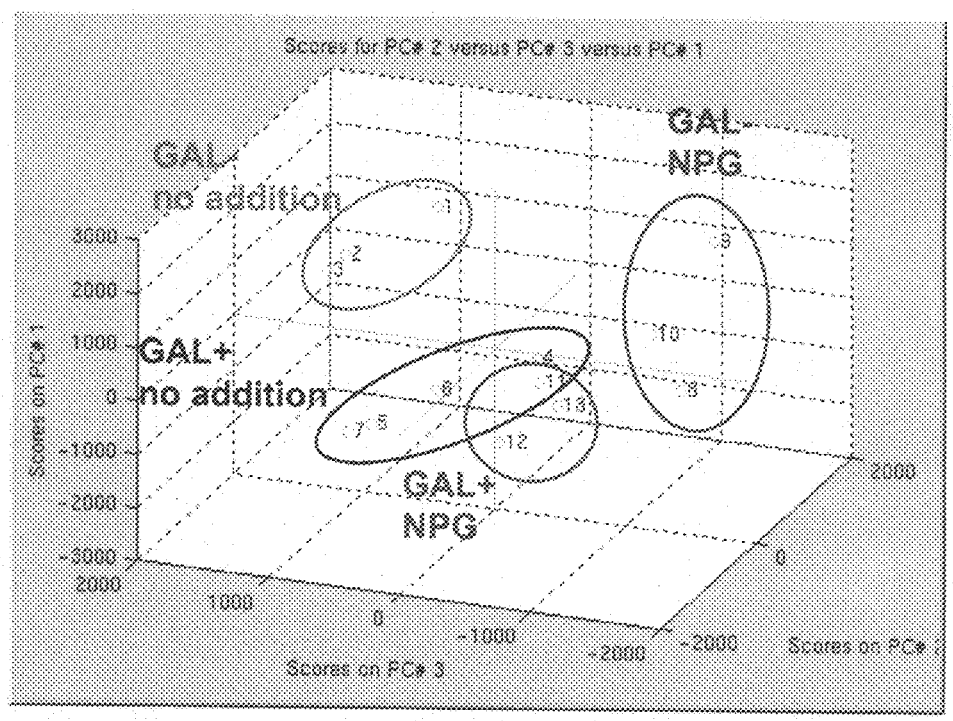

FIG. 9 shows a Principal Components scores plot generated from ToF-SIMS data of $E.$ $coli$ β-galactosidase/NPG samples.

Figure 10:
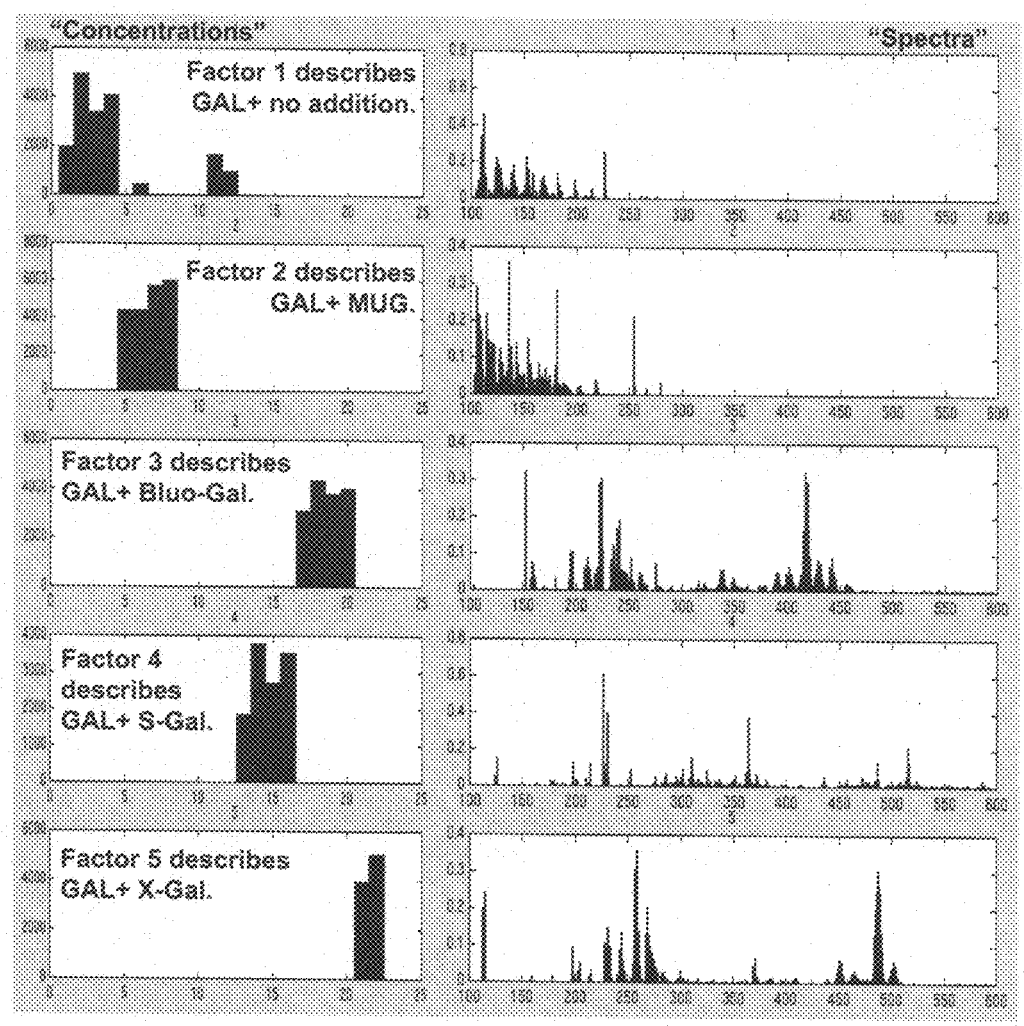

FIG. 10 shows results of Principal Components Analysis and Multivariate Curve Resolution applied to ToF-SIMS data from $E.$ $coli$ β-galactosidase+reactant samples. Shown are concentrations and computed spectra for each of five factors that emerge from the data analysis.

Figure 11:
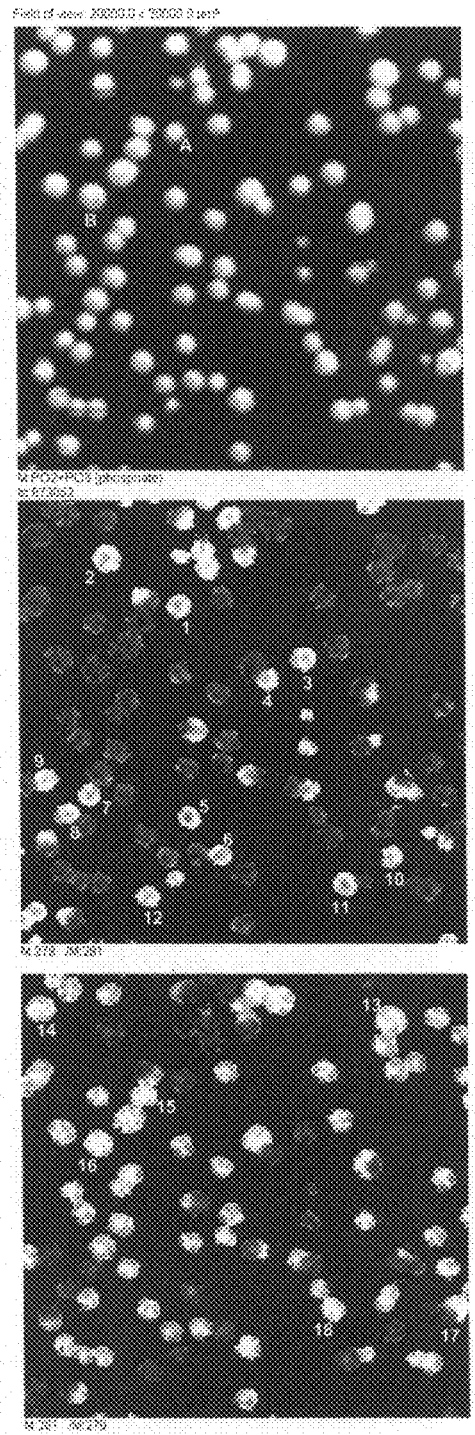
Figure 11D:
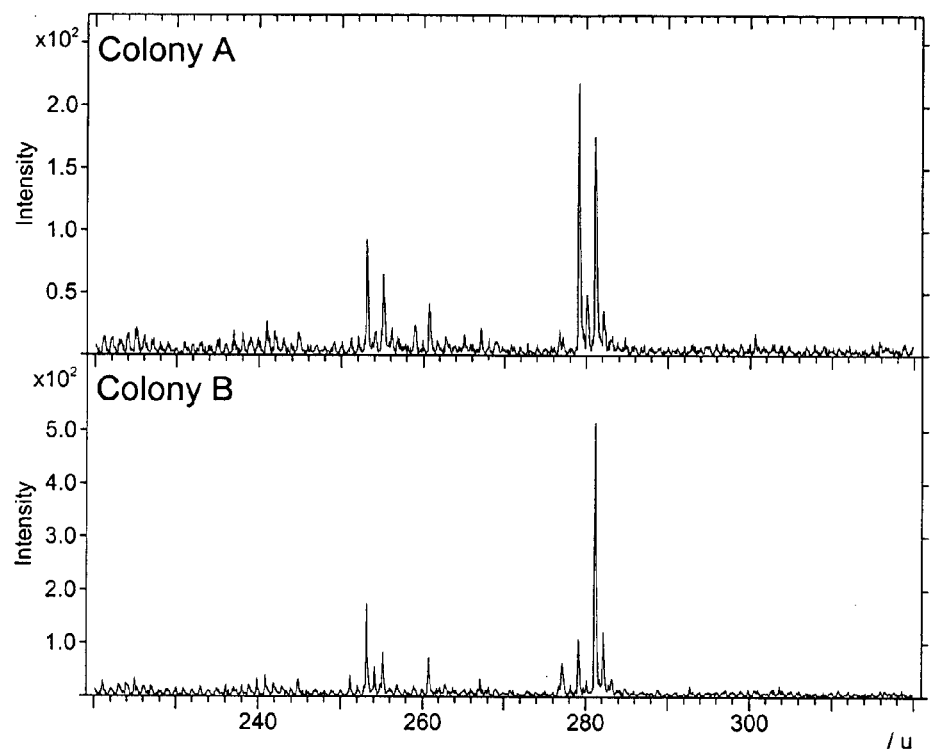

FIGS. 11A-D shows a spatial distribution map produced from specific peak intensities from the TOF-SIMS mass spectral data at each pixel of an array of colonies. The three panels show the comparison of phosphate map (11A), ratio of (m/z 279)/(m/z 281) map (11B), and ratio of (m/z 281)/(m/z 279) map (11C), from the mixture of two different colony types (Q, Q+4). FIG. 11D shows the negative secondary ion spectra from pixels making up two different colony types (Q, Q+4) indicated by the "A" and "B" on the map of FIG. 11A.

Figure 12:
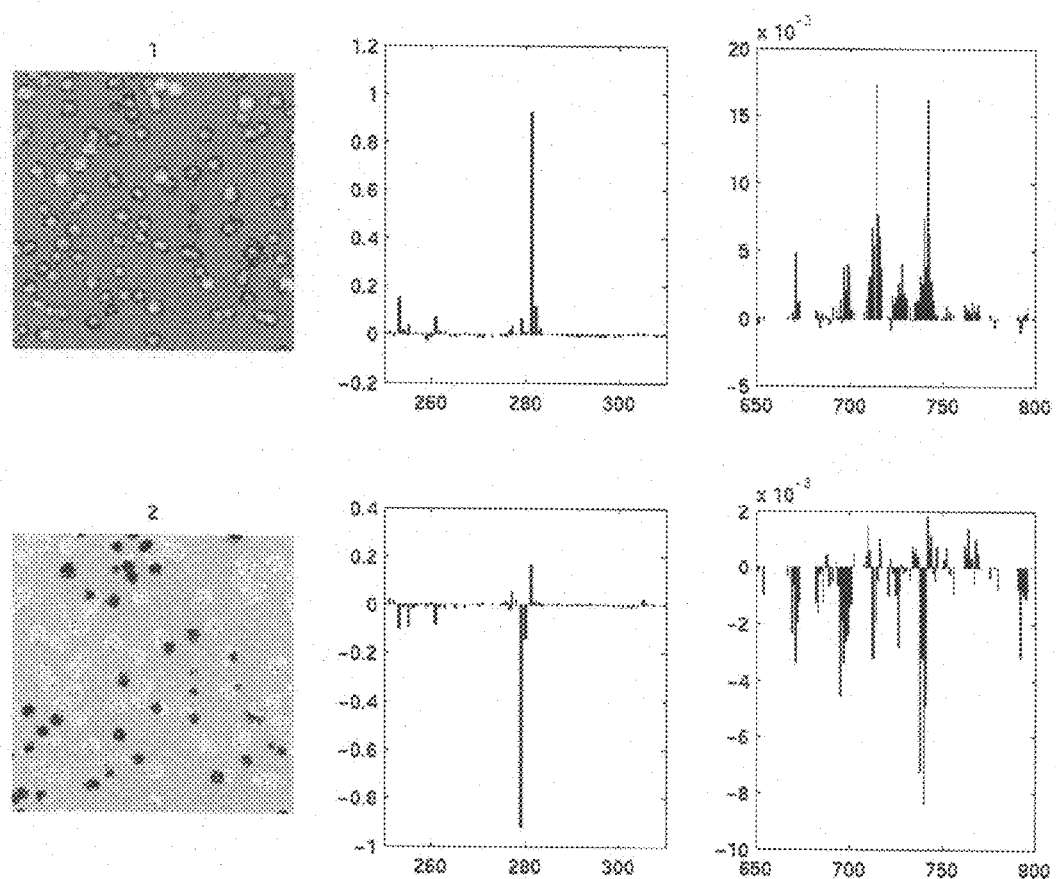

FIG. 12 shows the map locations and spectra of Principal Component 1 and Principal Component 2 derived from analysis of ToF-SIMS data from *Yarrowia* colonies.

Figure 13:
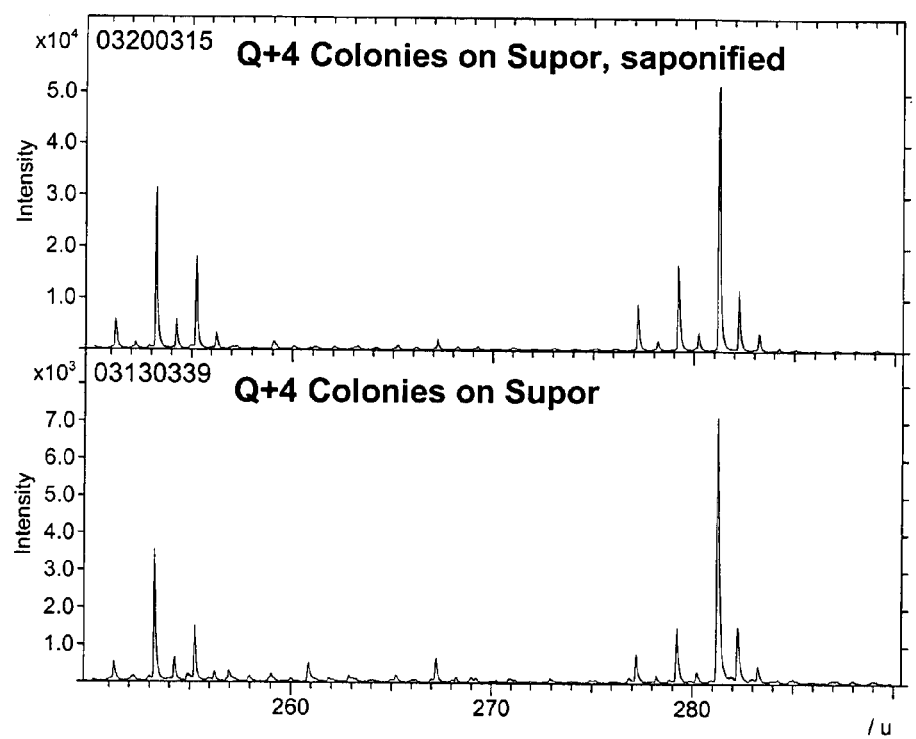

FIG. 13 shows the negative TOF-SIMS data: Q+4 colony grown on Supor® and Q+4 Colony on Supor® after undergoing saponification procedure.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 shows the 10.3 kb DNA fragment of the Q+4 *Yarrowia lipolytica* strain, for expression of four genes: a *Mortierella alpina* high affinity PUFA elongase, an *M. alpina* Δ5 desaturase, a *Saprolegnia diclina* Δ17 desaturase and an *M. alpina* Δ6 desaturase.

DETAILED DESCRIPTION OF THE INVENTION

The present invention describes a method for analyzing the contents of microorganisms using TOF-SIMS data collection and analysis, wherein the cells analyzed require no prior preparation, but are intact when introduced into the TOF-SIMS instrument. The invention further describes the TOF-SIMS analysis of colonies of microorganisms that are grown on vacuum compatible membranes, which are directly transferred to the TOF-SIMS instrument. The colonies are present in an array on the membrane and one aspect of the ToF-SIMS data is used to map the array of colonies. Other aspects of the ToF-SIMS data are used to identify differences in the contents of cells between colonies in the array on the membrane. Previous replication of the array of colonies then allows the rescue of individual colonies having a desired or distinguishing cell contents. By this method large numbers of individual colonies can be rapidly screened, such as colonies present in biological samples or collections, and mutant or gene-expression libraries. The following definitions may be used for interpretation of the claims and the specification.

"Time-of-Flight Secondary Ion Mass Spectrometry" is abbreviated TOF-SIMS.

The Term "TOF-SIMS detectable product" means any compound or substance that can be detected by the Time-of-Flight Secondary Ion Mass Spectrometry detection method. The TOF-SIMS detectable product may be a known specific compound that is derived from a provided reactant or is produced from a reactant that is present in the cell. Additionally the ToF-SIMS detectable product may not be defined, but cause a difference in the TOF-SIMS data between samples being compared.

"TOF-SIMS screening" refers to the process that is applied by the TOF-SIMS instrument to collect data from samples.

"TOF-SIMS analysis" includes collection of the data from the ToF-SIMS instrument and in addition, the manipulation of this data to produce information characterizing the samples assayed. TOF-SIMS analysis may include Principal Components Analysis (PCA) and Multivariate Curve Resolution (MCR).

A "mixed population" or "mixed population of cells" is a population of biological cells that includes multiple types of individuals. The individuals are of different types due to differences in cell contents. Mixed populations may comprise multiple strains of an organism, a mutant population, or other populations where there are differences among the individuals.

The term "array" when used in reference to the orientation of biological organisms on a substrate means a two dimensional distribution of organisms wherein the spatial orientation of the organisms is maintained.

To "raster" means to either steer the primary ion beam of a ToF-SIMS instrument over a pixel array spanning an area of the sample, or to move the sample under the (stationary) primary ion beam according to a pixel array spanning an area of the sample.

The term "vacuum compatible support" refers to a surface or membrane that is comprised of a material that is capable of withstanding a very low atmospheric pressure without deterioration. Additionally the vacuum compatible support must be a membrane on which an array of biological organisms may be placed in a manner such that spatial integrity of the organisms is maintained. Suitable materials include but are not limited to paper materials, and polymeric materials such as nylon, nitrocellulose, polyethersulfones, polysulfones, polycarbonate, polystyrene and silicon/silica, and glassy carbon.

An "aspect" of TOF-SIMS data is a portion of the entire ToF-SIMS data that by itself provides a set of information that can be used to characterize the sample assayed.

To "map the array" means to supply each individual in the array with a defined location. The defined location, called the locus, can be provided in a pictoral representation. TOF-SIMS data may be associated with each locus, and therefore with each individual in the mapped array.

"Chemometric methods" refers to mathematical or statistical methods that are used to relate measurements made on a chemical system to the state of the system. Chemometric methods are used to deconvolute complex sets of data to allow characterization of the samples from which the data is collected. Examples of chemometric methods include Principal Components Analysis (PCA) and Multivariate Curve Resolution (MCR).

A "primary product" is a substance that can itself be transformed, or is capable of transforming a reactant, into a TOF-SIMS detectable product. The primary product may be transformed by contact with another substance, such as transformation of a cellular component by acid or base hydrolysis. A primary product that is an enzyme may act upon a reactant to produce a TOF-SIMS detectable product.

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of C atoms and Y is the number of double bonds.

The term "chimeric gene" refers to any gene that contains: 1.) DNA sequences, including regulatory and coding sequences that are not found together in nature; or 2.) sequences encoding parts of proteins not naturally adjoined;

or, 3.) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature. "Transformation" refers to the transfer of a foreign gene or genes into the genome of a host organism.

"Promoter" refers to a nucleotide sequence, usually upstream (5') to a coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of an mRNA or functional RNA.

The "transcription terminator" means the 3' non-coding regulatory sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence (e.g. for a target gene, etc.).

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-lnterscience (1987).

Time-of-Flight Secondary Ion Mass Spectrometry (ToF-SIMS)

In the ToF-SIMS process a high-energy (8-25 kV), low-current (nanoamps DC, picoamps pulsed), pulsed primary ion beam bombards the surface of a material. Positively- and negatively-charged secondary ions are produced from the top monolayer (10-20 Angstroms). These secondary ions are analyzed and detected by a mass spectrometer. The mass spectra yield information on surface composition and structure. The invention is the first application of this surface bombardment analysis to cells that are intact upon placement in the TOF-SIMS instrument.

In the "static" SIMS regime, the low primary ion beam current and the random beam raster ensure that undamaged surface is sampled over the time of acquisition. This is in contrast to "dynamic" SIMS, in which the primary ion beam is used to sputter/remove material from the surface and data is acquired as a function of depth. In static SIMS, high-mass molecular secondary ions can be detected, whereas in dynamic SIMS, molecular information is destroyed, and only elemental or low-mass information is obtainable. The static SIMS regime is most useful for the invention since the high-mass molecular information obtained is able to identify many products in the cell, whereby differences can be used to distinguish cells.

Types of mass spectrometer that have been used for secondary ion analysis and detection include quadrupole mass spectrometers, magnetic sector mass spectrometers, and time-of-flight mass spectrometers. Quadrupole mass spectrometers are limited by mass range (generally less than 2000 m/z) and mass resolution (generally around unit mass resolution). Magnetic sector mass spectrometers offer very high mass resolution, but require tuning specific to the mass range of interest. Both quadrupole and magnetic sector spectrometer optics must be scanned in order to scan over the mass range. Time-of-flight mass spectrometers offer higher transmission of secondary ions which is independent of mass, and essentially parallel detection of masses, since the entire mass range is collected over a period of microseconds. Ions are separated by time required to traverse a field-free flight path, which is dependent on mass. For static SIMS analysis of organic materials, in which analysis time must be short in order to limit ion beam damage, the time-of-flight spectrometer is the spectrometer of choice.

Use of the time-of-flight principle alone results in only a moderate mass resolution of around 500 (m/dm). This is because secondary ions are emitted from the sample with a significant energy distribution. There are currently two different time-of-flight spectrometer geometries used for SIMS which employ different methods of energy focussing. These are known as the ion reflector type and the triple-focussing sector type. Although the examples included herein make use of ion reflector type ToF-SIMS instruments, a triple-focussing sector instrument is expected to provide similar results, and therefore could be used to practice the invention. For both types of time-of-flight spectrometers, the polarity of the extractor must be switched to collect either positively-charged or negatively-charged secondary ions. Thus "positive TOF-SIMS" spectra, referring to the signal from positively-charged secondary ions, and "negative TOF-SIMS" spectra, referring to the signal from negatively-charged secondary ions, are collected as separate acquisitions.

One problem that arises in the ToF-SIMS analysis of insulating materials such as ceramics or polymers, as occurs in the membranes used in the invention, is charging of the sample. The primary ion beam is typically positively-charged, and an insulating sample will immediately also acquire a positive charge. If not compensated for, this charging affects the extraction of secondary ions into the spectrometer. An electron flood gun is used to compensate for charge build-up on the sample.

If a time-of-flight mass spectrometer is used, the primary ion beam must be pulsed in order to determine a starting time. A typical duty cycle for analysis of an insulating sample starts with the primary ion beam pulse, followed by a period in which the secondary ion extraction voltage is on. The extraction voltage is switched off, after which the flood gun is switched on. After a length of time during which the highest mass secondary ions of interest have reached the detector (typically 100-200 microseconds), another duty cycle begins.

The primary ion sources used for ToF-SIMS have included noble gases (Argon, Xenon), Cesium, oxygen, silicon penta- and hexa-fluoride, and so-called "liquid metals" such as Gallium, Indium, and Gold. For mapping experiments in which the primary ion beam is rastered, liquid metal ion sources are required because of the intensity/brightness of these sources even when focussed to sub-micron size. A gold source has been developed recently which offers mapping capability with enhanced high-mass secondary ion signal, since this signal increases with mass of the primary ion. Au-1, Au-2, and Au-3 are accessible with this source. New primary ion sources, including new polyatomic primary ion sources, are continually under development. Any available source is applicable to the present invention where sources using Cesium, Gallium, or Au-1 as the primary ion source, are preferred.

ToF-SIMS is a semi-quantitative technique. Because the physical phenomena of ionization and desorption are coupled in the present invention, secondary ion yields depend on chemical environment or so-called "matrix effects." However, semi-quantitative or relative information ("more" vs. "less" or correlation to measured/end-use properties) is possible from a series of related samples through the use of peak area ratios. The area under a peak of interest (e.g., the molecular secondary ion of a known additive or product) is ratioed to the area under a peak chosen to serve as a reference. As an example, a relative measure of silicone oil contamination on a Mylar®PET film surface may be obtained by comparing the ratio of the silicone oil peak area at m/z 147 (C3H9SiO—C2H6Si+) to the PET peak area at m/z 104 (C6H4CO+) from a series of Mylar*PET samples. If no clear reference peak exists or is known, the total positive or negative secondary ion yield or a portion of the same for that spectrum can be used as reference. This process of using ratios within the TOF-SIMS data as a basis for distinguishing samples with different properties is known to one skilled in the art and is useful in practicing the invention as demonstrated in Example 2, where the ratio of indigo molecular ion area to total positive secondary ion yield is used as a relative measure of indigo production over a number of colonies analyzed.

ToF-SIMS data can be further evaluated using chemometrics. As defined by by B. M. Wise and N. B. Gallagher in the PLSToolbox reference manual (PLS_Toolbox Version 2.0, copyright 1998, Eigenvector Research, Inc., Manson, Wash., page 31): "Chemometrics is the science of relating measurements made on a chemical system to the state of the system via application of mathematical or statistical methods". ToF-SIMS data is multivariate; "multivariate" describes data that consists of measurements of many variables per sample. In the case of TOF-SIMS mapping data, each mass channel can be considered a variable, and intensities for each of these many variables is collected for each pixel in a mapping array. Another sense of the multivariate nature of TOF-SIMS is the existence of multiple spectral patterns from different chemical species making up the total positive or negative ToF-SIMS spectrum.

Two factors inherent in the SIMS technique make the use of multivariate statistical techniques known to those skilled in the art such as Principal Components Analysis (PCA) and Multivariate Curve Resolution (MCR) helpful in the interpretation and extension of SIMS data. One factor is that, unlike other analytical techniques involving mass spectrometry, such as GC-MS (Gas-Chromatography-Mass Spectrometry), there is no separation of species prior to entrance of secondary ions into the mass spectrometer. The mass spectral data is a convolution of secondary ion patterns from all species coexisting on the surface, and many low-mass hydrocarbon peaks are generic or common to many species. The second factor is that, in a mapping experiment in which the primary ion beam is rastered over an area of the surface, the concentration of current in the focussed spot causes higher incidence of charging and beam damage. The end result is much lower signal-to-noise for the mass spectral data acquired in this mode.

In a typical mapping experiment, TOF-SIMS spectral data are acquired at each pixel of a 256×256 pixel array spanning an analysis area. Principal Components Analysis takes this set of 65536 spectra and attempts to first look for what constitutes variance in the data, and then re-categorizes the data in terms of principal components that capture successively smaller amounts of this variance. In doing this, PCA is essentially grouping together pixels with similar spectral patterns. As noted earlier, both positive TOF-SIMS and negative ToF-SIMS mapping data can be acquired in separate data runs. The negative and positive mapping data may be analyzed separately by Principal Components Analysis or, if pixel registration between the positive and negative data can be achieved, may be analyzed as one combined set of spectra.

The results of a Principal Components Analysis are dependent upon the pre-processing of the data. It is a common practice of those skilled in the art to use data which has been mean-centered. In mean-centering, the mean for each column, which represents intensities at one particular mass channel for all pixels, is subtracted from each entry in that column. In addition, for all examples described herein using Principal Components Analysis, the set of pixel spectra (65536 for a 256×256 array) were normalized prior to mean-centering. This generally means normalizing to total ion yield or a subset of the total ion yield as noted in the examples.

Multivariate Curve Resolution is a way of separating data which is a composite of many contributing factors into its separate factors. The output of PCA may be used as a starting point for MCR to further reduce the ToF-SIMS data to information about specific chemical species. One skilled in the art will be familiar with these techniques as discussed in the PLS_Toolbox tutorial (PLS_Toolbox, Version 2.0, Eigenvector Research, Inc., Manson, Wash.), and would be able to practice them for use in this invention.

TOF-SIMS Detectable Products

The nature of the TOF-SIMS technique requires certain conditions be met in order for a chemical species to be detected:

TOF-SIMS is carried out in ultra-high-vacuum ($<1\times10^{-9}$ torr pressure). The species to be detected must thus be vacuum-compatible.

The compound of interest must present itself at the outermost 10-20 Angstroms of the sample analyzed.

The compound must yield secondary ion peaks or a spectral pattern that distinguishes it from the secondary ion signal arising from all the other species contributing to the overall spectrum.

Within these limitations there are a large number of substances that may be detected by TOF-SIMS. Biological substances that may be detected include many components of a living cell. Some examples include, but are not limited to, fatty acids, proteins, carbohydrates, and organic acids. Fatty acids are preferred compounds for detection using the method of the instant invention and may include lauric, myristic, palmitic, or stearic acid; oleic acid, linoleic acid, linolenic acid, di-homo-gamma linoleic acid, arachidonic acid, stearidonic acid, eicosatetraeneoic acid, eicosapentaenoic acid, docosahexaenoic acid, hydroxy fatty acids, peroxy fatty acids, branched chain fatty acids, and also compounds containing substituent fatty acids such as phospholipids and phospholipid fragments, triglycerides and triglyceride fragments.

Some cellular components may not be readily TOF-SIMS detectable in their native state, but may be converted to ToF-SIMS detectable products through a reaction that is mediated by an externally supplied substance. For example, acid or base treatments may be easily applied to cells to convert some cellular components. An example is saponification of triacylglycerides and phospholipids using sodium hydroxide. Methanol together with potassium hydroxide is a common treatment for saponification. Potassium hydroxide alone is a preferred saponification treatment for use in the instant invention. Treatments such as these, that may be applied to colonies on a membrane wherein colony integrity is maintained, may be used in the practice of the invention.

Also TOF-SIMS detectable products may be made by living cells from reactants supplied to the cells. Reactants may be natural substances such as amino acids or various sugars, or reactants may be especially synthesized compounds that are designed to be converted by specific cellular processes. For example, X-Gal (Holt, S. J., and P. W. Sadler. Proc. Royal Soc. (London) 148B: 495 (1958)) was designed to be converted by the β-galactosidase enzyme to a product that is visually detectable. However, ToF-SIMS allows the detection of many substances as described above, that are not visually detectable.

The time-of-flight spectrometer theoretically has no mass limit. However, since desorption from the surface is part of the process, there is a finite radius of influence of the primary ion beam which limits the size, and therefore the mass, of secondary ions that can be desorbed. Thus the TOF-SIMS detectable products are generally equal to or less than 8 kD Organisms for TOF-SIMS Analysis Organisms to be analyzed using TOF-SIMS in the present invention include any eukaryotic and prokaryotic organisms that can be applied to a membrane support and introduced into the TOF-SIMS instrument. It is preferred if the organisms are applied to the membrane support such that individuals are separated from each other. Organisms that grow as colonies are particularly suitable for the practice of this invention and include, but are not limited to, species of yeast such as *Saccharomyces, Picchia*, and *Yarrowia*; gram negative and gram positive bacteria such as *Rhodococcus, Streptomyces, Actinomycetes, Corynebacterium, Bacillus, Escherichia coli, Pseudomonas, Salmonella*, and *Erwinia*. Also included may be fungi such as *Penicillium, Fusarium, Aspergillus, Podospora, Chrysosporium, Trichoderma*, and *Neurospora*. Cells derived from eukaryotic organisms that can be grown in culture following the above criteria including mammalian cell lines and primary cultures, and plant cells such as from maize, rice, wheat, soybean, tobacco, and arabidopsis may also be used to practice the invention.

Samples of organisms for analysis may be from environmental, clinical, food, experimental or other sources. The TOF-SIMS method of the present invention may be used to identify contaminants or pathogens present in samples based on ToF-SIMS detectable distinguishing components present in the contaminant or pathogen cells. Preferably fatty acid components detected by ToF-SIMS are used to identify bacterial species where distinguishing fatty acids exist.

Vacuum Compatible Supports

The vacuum environment and surface specificity of the TOF-SIMS technique are important considerations in the selection of a vacuum compatible support (such as a membrane) required for practice of the invention. The membrane must be compatible with a low pressure vacuum environment and it must have an absence of surfactants or other surface-mobile agents or additives. It is preferred if the membrane is also compatible with the growth of organisms, and porous to support growth of the organisms when placed on the surface of a culture medium. Any membrane meeting these requirements can be used, such as membranes of polyethersulfone, polysulfone, nylon, polycarbonate, or nitrocellulose (washed with solvent to remove surfactant). Colonies may also be transferred from growth medium or a membrane supporting growth onto other types of membranes compatible with the TOF-SIMS instrument, such as silicon wafers or glassy carbon plates. The silicon wafer should have low resistivity and be considered conductive, and the orientation or dopant thickness may vary, such as having Boron or phosphorus and 110 or 111 orientation.

Replicate Organism Samples

Colonies of organisms grown on the surface of a medium can be replicated with maintenance of their original spatial orientation. A filter or membrane that is placed on top of the colonies on the surface will pick up some cells from each original colony. When the second filter or membrane is placed on a growth medium and incubated under growth conditions, the cells divide and form a replica of the original colony set. Any number of replicas may be made from the original set of colonies, or from any subsequent replicated set. Colonies may be replicated from one filter or membrane to another in the same manner. Replication of a set of organisms allows one set to be maintained, while another set is analyzed in a destructive fashion. As long as the orientations of the maintained and analyzed colony sets can be aligned, individuals identified with specific properties from the analysis may be propagated.

Individual Organisms in Mixed Populations

Growth of colonies of organisms on a surface establishes a spatial distribution, or array, of individuals. When the colonies are grown on a filter or membrane support, they may be transferred while maintaining their spatial distribution. Transfers to different media, to solutions and to experimental instruments are all useful to the practice of this invention.

The maintenance of the array of individuals within a mixed population allows the identification of specific individuals with differing characteristics. The mixed population may be composed of mostly identical individuals with respect to a characteristic, with one or a few different individuals. The mixed population may contain different individuals with multiple differences in characteristics.

Screening Populations

Screening of mixed populations to identify individuals with desired characteristics is used in programs involving mutagenesis, gene shuffling, or other methods of altering the genetic make-up of organisms. The large mixed populations containing genetically altered individuals are generally called libraries. Screening of thousands, or even many thousands of individuals in a library may be necessary to identify a few individuals with desired characteristics. The method of the invention allows rapid and efficient screening of individuals directly on the membrane on which they are grown. In one embodiment the individuals on the membrane are directly assayed with no need for individuals to be transferred to microtitre plates or put through any processing steps. In another embodiment processing steps that can be applied directly to the membrane and do not disrupt the colony integrity are used. This invention is the first demonstration that TOF-SIMS, which is a surface analysis technique, can identify cellular components directly from colonies grown on a membrane support.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994) or by Thomas D. Brock in Biotechnology: A Textbook of Industrial Microbiology, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "sec" means second(s), "min" means minute(s), "hr" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "mg" means milligram(s), "pg" means microgram(s), "ng" means nanogram(s), "U" means unit(s), "µm" means micrometer(s), "cm" means centimeter(s), "mm" means millimeter(s), "RPM" means revolutions per minute, "bp" means base pair(s), "kb" means kilobase(s) and m/z means mass to charge ratio.

Example 1

ToF-SIMS Identification of *E. coli* Expressing β-galactosidase through Indigo Detection This example demonstrates the ability of ToF-SIMS to distinguish a bacterial colony that expresses the β-galactosidase enzyme from one that does not. It uses a system in which there is a clear visual change in those organisms able to convert reactant (colorless 5-bromo-4-chloro-3-indolyl-β-D-galactoside) to product (blue indigo derivative), allowing immediate verification of the TOF-SIMS data. This example also demonstrates a method for transferring a collection of bacterial colonies from solid growth medium to the high-vacuum analysis chamber of the ToF-SIMS instrument, while maintaining the spatial relationship of the colonies.

Test System:

The *Escherichia coli* lacZ gene encoding β-galactosidase (β-gal) is a classical histochemical reporter gene (Beckwith, J. R. Lac: The genetic system. In *The Operon*. J. H. Miller and W. S. Reznikoff, Eds. Cold Spring Harbor Laboratory: Cold Spring Harbor, N.Y. (1980)). Its activity can be detected using a variety of substrates, all of which have galactose linked through a β-D-glycosidic linkage to a moiety whose properties change upon liberation from galactose (Wallenfels, K., and R. Weil. In *The Enzymes*. P. D. Boyer, Ed. $3^{rd}$ ed. Academic:NY, 7:617 (1972)). One useful chromogenic substrate that yields a precipitated product upon cleavage by β-gal is the indole derivative, 5-bromo-4-chloro-3-indolyl-β-D-galactoside (or "X-gal"; Holt, S. J., and P. W. Sadler. *Proc. Royal Soc.* (London) 148B:495 (1958)). When β-gal cleaves the glycosidic linkage in X-gal, a soluble, colorless indoxyl monomer is produced. Subsequently, 2 of the liberated indoxyl moieties form a dimer that is nonenzymatically oxidized to yield a halogenated indigo that is a very stable and insoluble blue compound. Thus, it is possible to distinguish between *E. coli* cells that do and do not express lacZ, based on the presence or absence of the indigo product, respectively, when cells are grown in the presence of X-gal (commonly known as "blue/white" screening). Structurally, it is important to note that the indigo product of X-gal is maintained within the *E. coli* cell, thus this product is not secreted through the cellular membrane into the surrounding environment.

Preparation and Growth of *E. coli* Colonies on Nylon Membranes:

A petri dish containing ~20 mL LB agar with 100 µg/mL ampicillin was overlaid with 30 µL of 100 mM isopropylthiogalactoside (IPTG) in water and 50 µL of 20 mg/mL X-gal (5-bromo-4-chloro-3-indolyl-β-D-galactoside) dissolved in dimethylformamide, and the plate left open for 15 minutes for the surface to dry. A circle of microporous, positively charged, nylon 66 membrane cast on a polyester support, 0.45 µm pore size (Boehringer Mannheim, Mannheim, Germany) was placed on the surface of the agar, and a culture of *E. coli* DH5α transformed with a library of *E. coli* K12 genomic DNA in pUC18 was spread on top of the nylon membrane. This culture was previously determined to consist of a population where 34% of the plasmids had DNA inserts, and thus 34% of colonies grown from the culture were not expressing β-galactosidase due to interruption of the lacZ gene in pUC18 by the genomic DNA inserts ((Beckwith, J. R. Lac: The genetic system. In *The Operon*. J. H. Miller and W. S. Reznikoff, Eds. Cold Spring Harbor Laboratory: Cold Spring Harbor, N.Y. (1980)). After an overnight incubation at 37° C., the nylon membrane was covered with ~1500 colonies, 34% of which were white and the rest were blue. Blue colonies contained bacteria expressing β-galactosidase and so were able to convert the X-gal to an indigo derivative that was easily visualized (Holt, S. J., and P. W. Sadler. *Proc. Royal Soc.* (London) 148B: 495 (1958)).

Introduction of Colonies into the Vacuum Chamber for TOF-SIMS Analysis:

A 1 $cm^2$ section of the nylon membrane was cut out, peeled off of the growth medium, and mounted on a stainless steel circular sample holder (called the "puck") by screwing a Molybdenum mask over the membrane. The sample was then introduced into a PHI Model 7200 ToF-SIMS instrument (Physical Electronics, Eden Prairie, Minn.), per the manufacturer's instructions. Pump-down from atmosphere to $<1 \times 10^{-5}$ torr was accomplished in a pre-chamber, after which the sample stage was pushed through to the main analysis chamber using a magnetic transfer rod, where the pressure was $<1 \times 10^{-7}$ torr.

Figure 1:
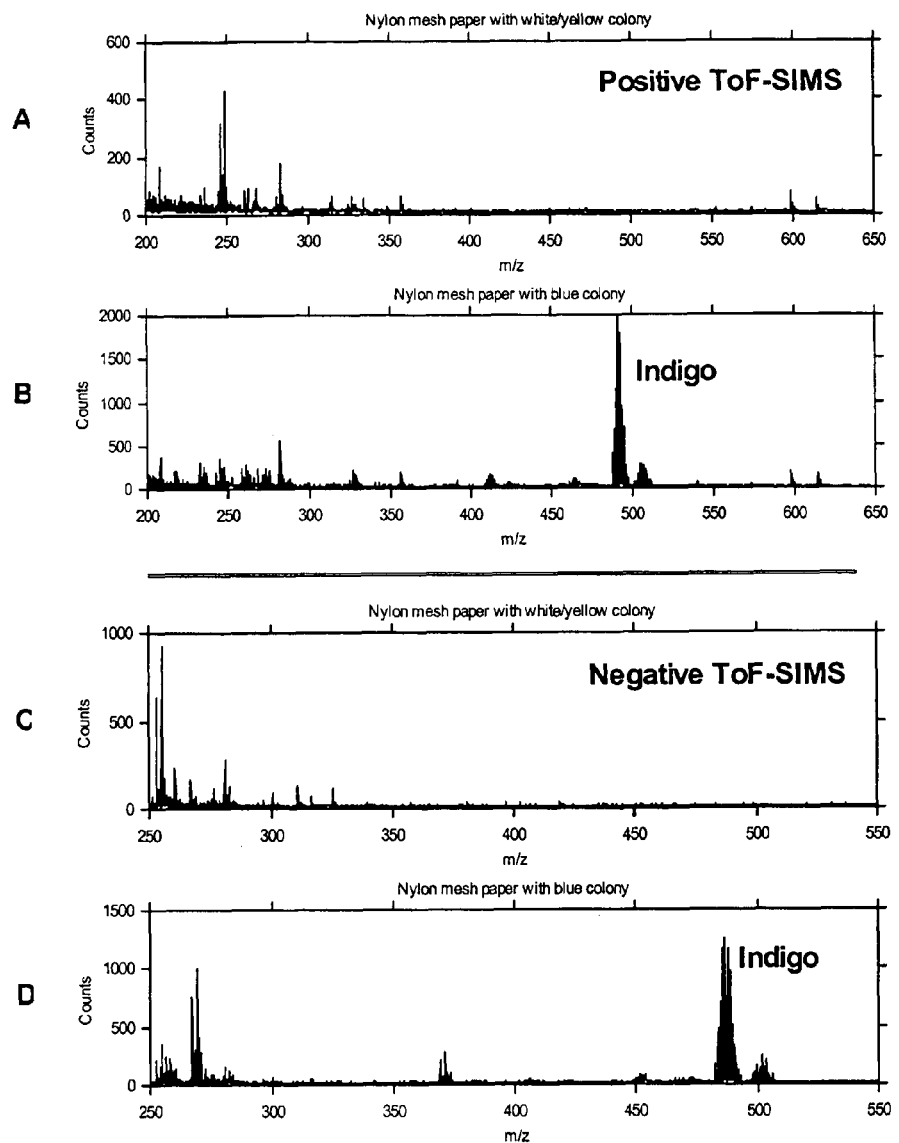

Confirmation of TOF-SIMS Detection of Blue Versus White Colonies, Based on Spectroscopic Differences A blue and a white colony were each screened by using the following TOF-SIMS conditions: a Cesium primary ion source, a pulsed electron flood gun for charge compensation, and a spectrometer of the ion reflector type. The area of each colony sampled was 200×200 µm². ToF-SIMS spectroscopic differences were detected between the two colonies. For the blue colony, ToF-SIMS data showed a cluster each of positively-charged and negatively-charged secondary ions at m/z 486 (FIG. 1B, D), the size of the protonated and deprotonated molecular ions, respectively, of the indigo derivative. The white colony showed no positively-charged or negatively-charged secondary ion clusters at m/z 486 (FIG. 1A, C). Thus, the ability of ToF-SIMS to identify a biological organism making a specific TOF-SIMS detectable product, the indole derivative of X-Gal, was demonstrated.

Example 2

Different Methods of TOF-SIMS Screening of Randomly-Arrayed Bacterial Colonies

The present Example describes three different methods for screening randomly-arrayed bacterial colonies, based on: 1.) acquisition of single-point spectra from known colony locations; 2.) mapping over a region containing multiple colonies by rastering the primary ion beam; and 3.) mapping over a region containing multiple colonies by rastering the sample stage under the primary ion beam. Using each methodology, E. coli colonies that did and did not produce a TOF-SIMS detectable product (e.g., the indole derivative of X-Gal) were identified in an array.

Colony Screening via Single-Point TOF-SIMS Analysis

As described in Example 1, a nylon membrane was prepared that was covered with a mixture of E. coli colonies including blue colonies expressing β-galactosidase and white colonies not expressing β-galactosidase. A sample of the membrane was transferred to the ToF-SIMS instrument as described in Example 1.

The sample stage coordinates for each of twelve colonies (a mixture of blue and white colonies) were determined by visual inspection of the membrane through the viewing eyepiece of the ToF-SIMS instrument with alignment to the micrometer scales, and recorded. The sample stage was moved to each set of coordinates in turn, and a 200×200 µm² area was screened for each colony separately, using the ToF-SIMS conditions described in Example 1.

Figure 2:
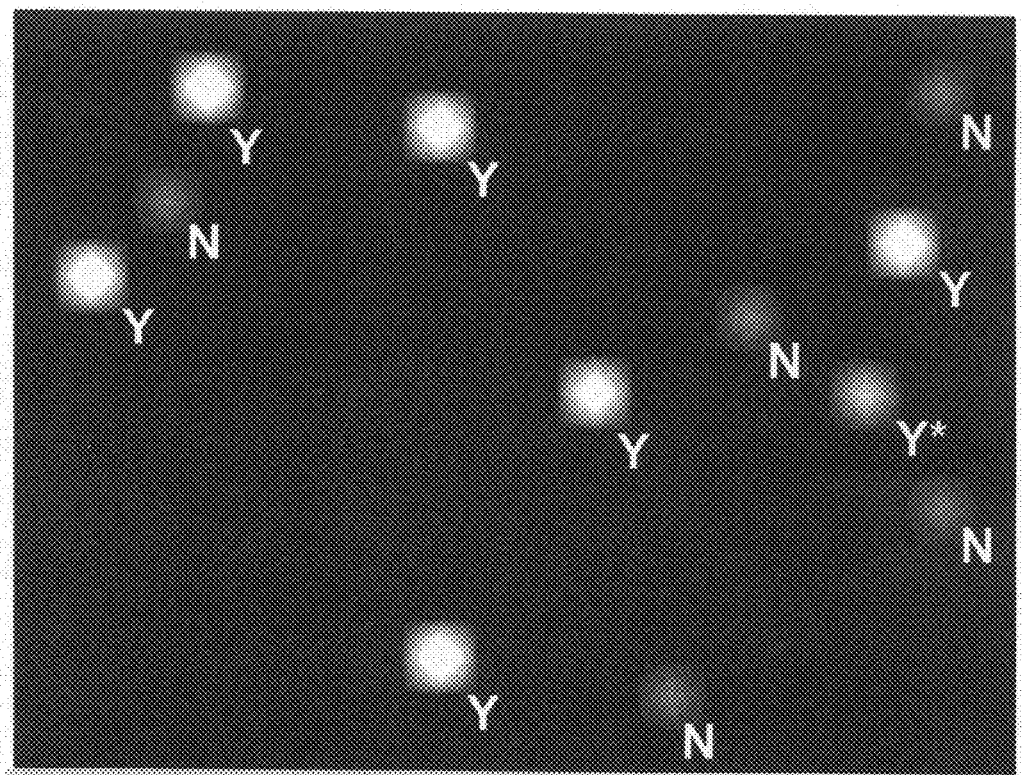
FIG. 2 shows a grayscale map of the ratios of the intensities of the TOF-SIMS positive molecular secondary ions characteristic of the indigo derivative to total secondary ion yield for each colony data set, pictured on a grid according to each colony's sample stage coordinates.

The intensities of the positive molecular secondary ions characteristic of the indigo derivative (as described in Example 1 and shown in FIG. 1) were ratioed to total secondary ion yield for each colony data set. The ratios were translated to a grayscale colormap and pictured on a grid according to each colony's sample stage coordinates. This colormap of the TOF-SIMS data in the format of the colony array showed six intensely white spots, one less intensely white spot, and five barely visible gray spots (FIG. 2). The seven white spots indicated the stage positions of seven colonies that contained the indigo derivative, while the five gray spots indicated colonies that did not contain the indigo derivative, as verified by the visual color of the colonies as blue and white, respectively.

Thus, a single-point TOF-SIMS analysis technique is useful for the identification of a biological organism making a specific TOF-SIMS detectable product.

Colony Screening via TOF-SIMS Secondary Ion Mapping via Primary Ion Beam Rastering and Chemometric Data Reduction As described in Example 1, a nylon membrane was prepared that was covered with a mixture of E. coli colonies including blue colonies expressing β-galactosidase and white colonies not expressing β-galactosidase. A sample of the membrane was transferred to the ToF-SIMS instrument as described in Example 1.

ToF-SIMS analysis was performed on a 400×400 µm² area of the membrane that included a portion of one blue colony and a portion of one white colony. A gallium primary ion beam with pulsed electron flood gun for charge compensation and a mass spectrometer of the ion reflector design was rastered at regular spatial intervals over the assay area with 256×256 pixel resolution. At each pixel, making up an array spanning the assay area, an entire surface mass spectrum was acquired.

Figure 3:
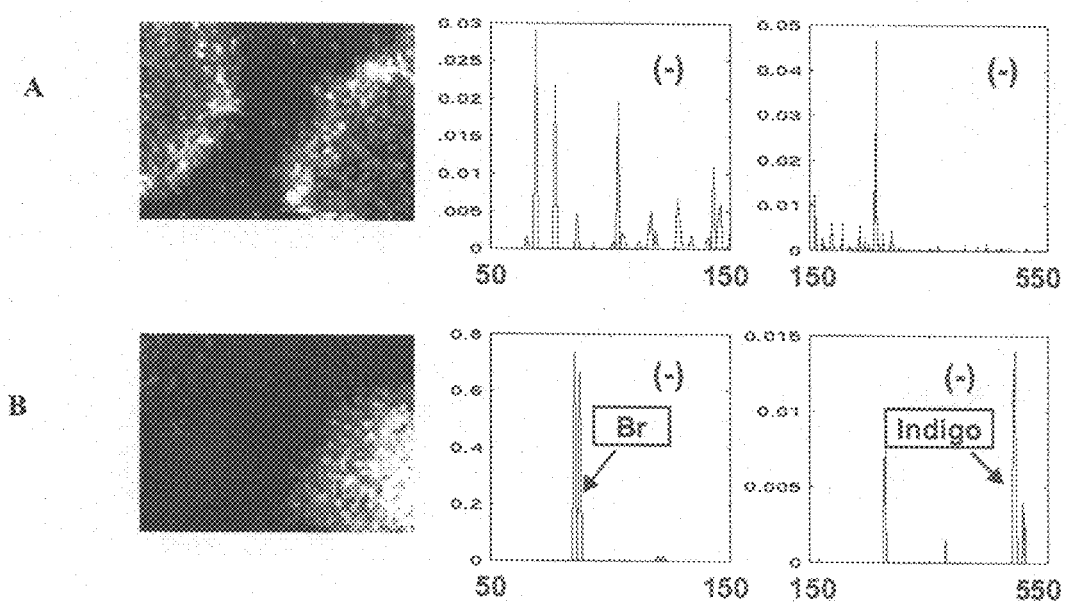
FIGS. 3A and 3B show results of Principal Components Analysis and Multivariate Curve Resolution applied to combined positive and negative TOF-SIMS data from X-Gal-fed $E.$ $coli$ colonies. The computed spectrum and spatial distribution of features are shown in A: common features; and B: indigo product.

The overall secondary ion signal obtained by rastering the primary ion source was lower than that obtained using the process described in Example 1, so a chemometrics data reduction method was used to enhance spectral contrast. The datafile was first clipped from 256×256 pixels to 204×256 pixels (320×400 µm²) so that it contained roughly equal portions of both colonies. The resulting set of 52,224 combined positive and negative TOF-SIMS pixel spectra were first normalized (to total positive secondary ion yield for the positive set and to total negative secondary ion yield from m/z 50 onwards for the negative set). This data set was then mean-centered and used as input for a Principal Components Analysis (PCA) (PLS_Toolbox Version 2.0, Eigenvector Research, Inc., Manson, Wash., in conjunction with MATLAB Version 5.3, The Mathworks, Inc., Natick, Mass.). The output of this analysis was then fed into a Multivariate Curve Resolution routine (PLS_Toolbox, MATLAB). This treatment, which is familiar to one skilled in the art, grouped pixels by similar spectral patterns and then separated out the spectral components. Two factors emerged. Spatial distribution maps were created by plotting the strength or "concentration" of each factor per pixel. One map showed the spatial distribution of those spectral features that were common to both colonies (FIG. 3A). Accompanying this map were the computed spectra for these common features. The second map (FIG. 3B) showed the spatial distribution of spectral features unique to one of the colonies. These unique spectral features were peaks corresponding to the bromine and indigo molecular secondary ions that were present in colonies expressing β-galactosidase. Verification of the colony with these features as being one expressing β-galactosidase was by its blue color.

A membrane was prepared that was covered with a mixture of E. coli colonies, including blue colonies expressing β-galactosidase and white colonies not expressing β-galactosidase, as described in Example 1 except that the membrane was a Supor® polyethersulfone membrane (Pall-Gellman, Ann Arbor, Mich.).

ToF-SIMS analysis was performed on a 500×500 µm² area of the Supor® membrane that included one blue colony, by primary ion beam rastering using an $Au_1$ gold primary ion beam and an $Au_3$ gold primary ion beam, with pulsed electron flood gun for charge compensation and a mass spectrometer of the ion reflector design (Ion-ToF Model ToF IV, Ion-ToF GmbH, Muenster, Germany). No chemometric data reduction was carried out on this data. The negative TOF-SIMS secondary ion maps from the gold ion beam data were able to detect the indigo directly as shown in FIGS. 4A and B, for $Au_1$ and $Au_3$, respectively. Bromine was also detected, as shown.

Thus, mapping via primary ion beam rastering and chemometric data reduction was a useful TOF-SIMS analysis technique for the identification of a biological organism making a specific ToF-SIMS detectable product.

Colony Screening via ToF-SIMS Secondary Ion Mapping via Stage Rastering under the Primary Ion Beam A membrane was prepared that was covered with a mixture of E. coli colonies, including blue colonies expressing β-galactosidase and white colonies not expressing β-galactosidase, as described in Example 1 except that the membrane was a Supor® polyethersulfone membrane (Pall-Gellman, Ann Arbor, Mich.). A sample of the membrane was transferred to the TOF-SIMS instrument as described in Example 1.

TOF-SIMS analysis was performed on a 20×20 mm² area of the membrane, including multiple colonies, with 256×256 pixel resolution by rastering the sample stage under a gold primary ion beam with pulsed electron flood gun for charge compensation and a mass spectrometer of the ion reflector design (Ion-ToF Model IV, Ion-ToF, GmbH, Muenster, Germany). At each interval, or pixel, making up the array spanning the area, an entire surface mass spectrum was acquired. Intensities of specific peaks from the mass spectral data at each pixel were then used to create a spatial distribution map. Specifically, the distribution of Chlorine, which tracks the membrane support, was used to produce a picture map of all of the colonies on the array as shown in FIG. 5A. The intensity of [phosphate+amide/CNO] secondary ions per pixel was also used to show the locations of all colonies as shown in FIG. 5B. The distribution of Bromine plus indigo molecular secondary ions was used to identify the locations of those colonies able to convert X-Gal to indigo as shown in FIG. 5C. Color overlays of Chlorine (blue)+[Phosphate+CNO] (red) or Chlorine (yellow)+[Bromine+Indigo] (blue) were used to easily identify the type of each colony. These secondary ion maps were compared to an optical picture of the colonies, which verified the identification of colonies that showed bromine and indigo molecular secondary ions by their blue color.

Thus, mapping via stage rastering under the primary ion beam was also a useful TOF-SIMS analysis technique for the identification of a biological organism making a specific TOF-SIMS detectable product.

Example 3

ToF-SIMS Detection of E. coli Expressing Phenylalanine; Ammonia Lyase

This example demonstrates ToF-SIMS detection in a system in which the product is a water-soluble low-molecular-weight organic acid, for which there is no visual change in those organisms able to convert reactant to product. This example also demonstrates a method whereby colonies able to produce product can be differentiated spectroscopically even when molecular secondary ions specific to product are not detected.

E. coli Expressing Phenylalanine:Ammonia Lyase:

To demonstrate TOF-SIMS detection of E. coli expressing an enzymatic activity that isn't as easily detectable as beta-galactosidase, we used a phenylalanine: ammonia lyase (PAL) from *Rhodosporidium toruloides* that had been mutated as described in U.S. Pat. No. 6,368,837. This enzyme had enhanced tyrosine:ammonia lyase (TAL) activity, however in the instant example only the PAL activity was assayed.

Phenylalanine ammonia-lyase (PAL) (EC 4.3.1.5) is widely distributed in plants (Koukol et al., *J. Biol. Chem.* 236:2692-2698 (1961)), fungi (Bandoni et al., *Phytochemistry* 7:205-207 (1968)), yeast (Ogata et al., *Agric. Biol. Chem.* 31:200-206 (1967)), and *Streptomyces* (Emes et al., *Can. J. Biochem.* 48:613-622 (1970)), but it has not been found in *Escherichia coli* or mammalian cells (Hanson and Havir in *The Enzymes*, 3rd ed.; Boyer, P., Ed.; Academic: New York, 1967; pp 75-167). PAL is the first enzyme of phenylpropanoid metabolism and catalyzes the removal of the (pro-3S)-hydrogen and —NH3+ from L-phenylalanine to form trans-cinnamic acid. Two strains of E. coli were compared in this example: E. coli BL21 (DE3) transformed with the pETAL construct, a pET-24d plasmid (Novagen, Madison, Wis.) containing the coding region for the EP18Km-6 mutant of the *Rhodosporidium toruloides* PAL enzyme (U.S. Pat. No. 6,368,837); and E. coli BL21 (DE3) transformed with the pET-24d plasmid (Novagen, Madison, Wis.). The latter strain served as a control with no detectable PAL/TAL activity.

Preparation and Growth of pETAL and pET-24d E. coli as Aqueous Cultures:

For growth of the pETAL and pET-24d strains in liquid culture, 5 mL of LB medium with 25 mg/L kanamycin and 1 mM IPTG was inoculated with either strain from a glycerol stock and grown overnight at 38° C. with shaking at 300 RPM. The following morning, when the O.D. (600 nm) of the cultures had reached ~2.0, the cultures were centrifuged at 10,000 RPM for 10 min and the pellets resuspended in either water or 4 mM phenylalanine which had been adjusted to ~pH 7 with KOH. These mixtures were further incubated at 38° C. and 1 mL aliquots withdrawn at 6 and 24 hrs. These were stored on ice prior to analysis by ToF-SIMS and HPLC.

Preparation and Introduction of Aqueous E. coli Culture Samples into the Vacuum Chamber for ToF-SIMS Analysis:

Ten µL of unfiltered, unmodified aqueous culture of pETAL grown for six hours and 24 hours with and without phenylalanine were each transferred to a clean Silicon wafer piece (Virginia Semiconductor, Fredericksburg, Va.) using an Eppendorf pipetting system. The droplet was allowed to evaporate in air, after which the silicon wafer piece was mounted on a stainless steel circular "puck" and introduced into a PHI Model 7200 TOF-SIMS instrument (Physical Electronics, Eden Prairie, Minn.), as described previously.

ToF-SIMS Detection of Cinnamic Acid Product from pETAL Aqueous Cultures:

The size of each evaporated aqueous culture droplet on the Silicon wafer was on the order of 5 mm in diameter. A 200× 200 µm² area of the dried droplet was screened using a Cesium primary ion source, a pulsed electron flood gun for charge compensation, and a spectrometer of the ion reflector type. The negative ToF-SIMS data from the six-hour and 24-hour phenylalanine-fed cultures showed a molecular secondary ion at m/z 164 that represented the phenylalanine (FIG. 6 B, D) and a molecular secondary ion at m/z 147 that represented the cinnamic acid product from TAL enzyme conversion of phenylalanine. The intensity of the cinnamic acid ion peak relative to the phenylalanine ion peak was greater for the 24 hour culture than for the six hour culture. Neither ion at m/z 164 or 147 was found in the six-hour and 24-hour cultures not fed phenylalanine (FIG. 6 A, D).

HPLC Detection of Cinnamic Acid Product from pETAL Aqueous Cultures:

The aqueous cultures of pETAL and pET-24d that had been resuspended in phenylalanine and incubated for 6 or 24 hours were subjected to HPLC analysis for cinnamic acid production. 0.1 mL of each aqueous mixture was microfuged for 10 min to remove the cells and 10 µL of the the supernatant was injected into a Hewlett-Packard model 1050 HPLC equipped with a Zorbax ODS column (3 µm particle, 6.2 mm×8 cm column), and developed over 10 min with a linear gradient of acetonitrile in water, both containing 0.1% formic acid (5% acetonitrile to 80% in 10 min). Cinnamic acid was detected by uv absorption and quantitated by comparison to a cinnamic acid standard (Sigma Chemical, St. Louis, Mo.).

The 6 hr aqueous culture of pETAL contained 0.9 mM cinnamic acid, and the 24 hr sample contained 1.6 mM. No cinnamic acid could be detected in either sample from the pET-24d culture. Thus the HPLC detection of cinnamic acid correlated with the ToF-SIMS detection of cinnamic acid in the 6 and 24 hr samples of pETAL.

Preparation and Growth of pETAL and pET-24d E. coli Colonies on Supor® Polyethersulfone Membranes:

Petri plates (10 cm diameter) of LB agar containing 25 mg/L kanamycin were spread with 30 μL of 100 mM IPTG, allowed to air dry for 5 min and then overlaid with a 90 mm circle of Supor®) polyethersulfone membrane. Glycerol Stocks of PETAL and pET-24d cultures were diluted sufficiently to result in ~600 colonies per plate, and a pure pETAL, pure pET-24d, and a 1:1 mixture were each spread over the surface of a membrane. After growth overnight at 38° C., a membrane with each type of colony on top was transferred to agar containing 4 mM phenylalanine adjusted to pH 7 with KOH, and incubated further at 38° C. for 24 hr.

Introduction of Colonies into the Vacuum Chamber for TOF-SIMS Analysis:

A 1 cm$^2$ section of each Supor® polyethersulfone membrane for analysis was in turn cut out, peeled off of the growth media and mounted on a stainless steel circular "puck" by screwing a Molybdenum mask over the membrane. The sample was then introduced into a PHI Model 7200 TOF-SIMS instrument (Physical Electronics, Eden Prairie, Minn.), as described previously.

TOF-SIMS Differentiation of pETAL vs. pET-24d Colonies, Based on Spectroscopic Differences:

On the membrane with the mixture of pETAL and pET-24d colonies that had been transferred to medium containing phenylalanine, eleven individual colonies were screened using a Cesium primary ion source, a pulsed electron flood gun for charge compensation, and a spectrometer of the ion reflector type. The area sampled for each colony was 200×200 μm$^2$.

Figure 7:
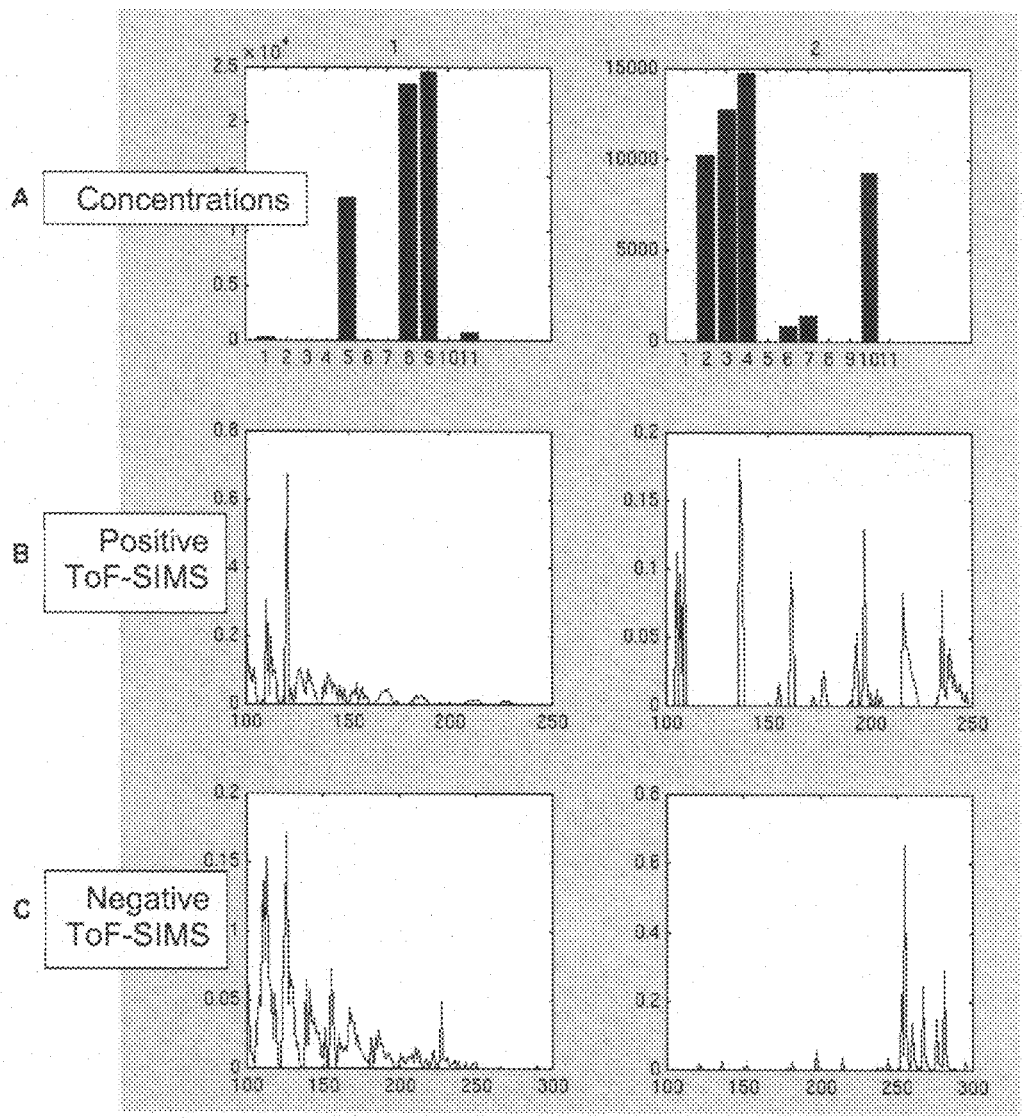

The cinnamic acid negative molecular secondary ion at m/z 147 was not observed in ToF-SIMS spectra acquired from pETAL colonies grown on the polyethersulfone membrane. The positive and negative ToF-SIMS data were mean-centered and used as input for a Principal Components Analysis (PCA) (PLS_Toolbox Version 2.0, Eigenvector Research, Inc., Manson, Wash., in conjunction with MATLAB Version 5.3, The Mathworks, Inc., Natick, Mass.). The output of this analysis was then fed into a Multivariate Curve Resolution routine (PLS_Toolbox, MATLAB). This treatment, which is familiar to one skilled in the art, identified factors representing variance in the spectral data. Factor 1 and Factor 2 showed different strengths, or "concentrations", for the eleven colonies screened (FIG. 6A). Specifically, colonies 1, 5, 8, 9, and 11 were described to different degrees by Factor 1and not by Factor 2, while colonies 2, 3, 4, 6, 7, and 10 were described to different degrees by Factor 2 and not by Factor 1. The negative TOF-SIMS computed spectra associated with these two factors showed major spectral differences in fatty acid distribution, between about 150 and 350 m/z (FIG. 7 B, C). Therefore the TOF-SIMS data identified two characteristically different colony types.

The same analysis was performed on pETAL and pET-24d colonies grown on separate polyethersulfone membranes that had been transferred to medium with phenylalanine. In the collected data, pETAL colonies were described by Factor 2 and pET-24d colonies were described by Factor 1. In addition, the negative TOF-SIMS data from pETAL and pET-24d colonies showed the spectral patterns indicated by Factor 2 and Factor 1, respectively. Thus colonies producing cinnamic acid and colonies not producing cinnamic acid were distinguished when grown on membranes in separate populations, and also when in a combined, arrayed population of organisms. TOF-SIMS was able to differentiate between E. coli engineered to produce a low-molecular weight, water-soluble product (cinnamic acid), even without direct detection of product signal.

Example 4

ToF-SIMS Detection of Five β-galactosidase-Cleaved Products in E. coli

This example demonstrates the utility of TOF-SIMS screening for a range of products ynthesized by E. coli based on β-galactosidase-cleavage of reactants. Products included methyl umbelliferone (MU) made from the cleavage of 4-methylumbelliferyl-β-D-galactopyranoside (MUG)(Sigma, St. Louis, Mo.) and ortho-nitrophenol (NP), made from the cleavage of 2-nitrophenyl-β-D-galactopyranoside (2NPG) (Sigma, St. Louis, Mo.), as well as the metabolites of 3,4-cyclohexeneoesculetin-β-D-galactopyranoside (S-Gal; Sigma, St. Louis, Mo.), 5-bromo-3-indolyl-β-D-galactopyranoside (Bluo-Gal; Sigma, St. Louis, Mo.), and X-Gal (Sigma, St. Louis, Mo.). MU, NP, and the S-Gal product are similar in molecular weight and solubility to cinnamic acid. Also demonstrated is the ability to differentiate E. coli expressing β-galactosidase (GAL) from E. coli not expressing GAL, without the need to provide a reactant.

Preparation and Growth of E. coli Colonies on Supor® Polyethersulfone Membranes for Production of β-galactosidase Products:

Pure cultures of E. coli expressing β-galactosidase activity ("GAL$^+$") and E. coli without β-galactosidase activity ("GAL$^-$") were were prepared from the E. coli library described in Example 1 by picking a single blue (GAL$^+$) and a single white (GAL$^-$) colony, inoculating 5 mL of liquid LB culture medium supplemented with 100 μg/mL ampicillin and grown overnight at 37° C., shaking at 300 RPM. These cultures were separately verified to be purely GAL$^+$ or GAL$^-$ by plating on LB media with ampicillin, IPTG and X-Gal as described in Example 1. The GAL$^+$ and GAL$^-$ cultures were spread separately onto Supor® polyethersulfone membranes in contact with growth media. The basic growth medium consisted of ~20 mL LB agar with 100 μg/mL ampicillin overlaid with 30 μL of 100 mM isopropylthiogalactoside (IPTG) in water. For each E. coli strain, one membrane was prepared on growth medium lacking any reactant, and one membrane was prepared on growth media containing each of the five reactants. When the reactants were added, 40 μL of solution was overlaid on the basic medium and allowed to air dry for 15 minutes. X-gal (20 mg/mL), Bluo-Gal (20 mg/mL), MUG (10 mg/mL), and 2NPG (50 mg/mL) were dissolved in dimethylformamide. S-Gal (20 mg/mL) was dissolved in water. The plates were incubated overnight at 38° C.

Introduction of Colonies into the Vacuum Chamber for TOF-SIMS Analysis:

For each array a 1 cm$^2$ section of the Supor® polyethersulfone membrane was cut out, peeled off of the growth media and mounted on a stainless steel circular "puck" by screwing a Molybdenum mask over the membrane. The sample was then introduced into a PHI Model 7200 ToF-SIMS instrument (Physical Electronics, Eden Prairie, Minn.), as described previously.

TOF-SIMS Differentiation of *E. coli* with and without β-galactosidase, Fed and not Fed MUG, or NPG:

Three or four colonies on each array of *E. coli* GAL⁺–no reactant, *E. coli* GAL⁺+MUG, *E. coli* GAL⁻–no reactant, and *E. coli* GAL⁻+MUG were screened using a Cesium primary ion source, a pulsed electron flood gun for charge compensation, and a spectrometer of the ion reflector type. The area sampled for each colony was 200×200 μm². The negative ToF-SIMS data was normalized and mean centered, then used as a dataset for Principal Components Analysis (PCA) (PLS_Toolbox, Eigenvector Research, Inc., Manson, Wash.), as known by one skilled in the art.

The PCA gave a score for each principal component for each sample, which represented the importance of each principal component for each sample. The scores for principal components #1, 2, and 3 for each colony were plotted in a three-dimensional map (FIG. 8). In this Figure a circle was drawn around the set of 3-4 colonies for each type of *E. coli* and reactant conditions. There was no overlap between circles, which indicated that the data differentiated between the colony sets. TOF-SIMS distinguished:

*E. coli* that expressed β-galactosidase enzyme from *E. coli* that did not, when both had been fed MUG reactant.

*E. coli* that expressed β-galactosidase enzyme from *E. coli* that did not, even if no reactant had been introduced.

*E. coli* that expressed β-galactosidase enzyme that had been fed MUG reactant from *E. coli* that expressed β-galactosidase enzyme that had not been fed MUG reactant.

Thus the differentiation between *E. coli* that expressed β-galactosidase enzyme from *E. coli* that did not, occurred in the presence and in the absence of MUG reactant.

Three or four colonies on each array of *E. coli* GAL⁺+NPG, and *E. coli* GAL⁻+NPG were screened with the same TOF-SIMS conditions above. This data was combined with the data from the *E. coli* GAL⁺–no reactant and *E. coli*–GAL⁻–no reactant data above and analyzed as above. Principal components #1, 2, and 3 for this dataset (different from the Principal components #1, 2, and 3 above) were plotted as above (FIG. 9). TOF-SIMS data distinguished:

*E. coli* that expressed β-galactosidase enzyme from *E. coli* that did not, when both had been fed NPG reactant.

*E. coli* that expressed β-galactosidase enzyme from *E. coli* that did not, even if no reactant had been introduced.

Thus the differentiation between *E. coli* that expressed β-galactosidase from *E. coli* that did not occurred in the presence and in the absence of the NPG reactant. The circles around the sample sets for *E. coli* that expressed β-galactosidase enzyme that had been fed NPG reactant and *E. coli* that expressed β-galactosidase enzyme that had not been fed NPG reactant overlapped, indicating that ToF-SIMS did not differentiate between these colony types. This result was explained since the product of the β-galactosidase enzyme reaction with NPG is 2-nitrophenol, which is not vacuum stable and was expected to be pumped away as soon as it was produced. The fact that PCA of the TOF-SIMS data confirmed this expectation supported the value of the ToF-SIMS analysis.

Two to four colonies on each array of *E. coli* GAL⁺+S-Gal, and *E. coli* GAL⁺+Bluo-Gal, and *E. coli* GAL⁺+X-Gal were screened with the same TOF-SIMS conditions above. The negative ToF-SIMS data was combined with the negative ToF-SIMS data from the *E. coli* GAL⁺ no reactant, *E. coli* GAL⁺+MUG, and *E. coli* GAL⁺+NPG data above and analyzed as above. The negative TOF-SIMS data was normalized and mean centered, then used as input for Principal Components Analysis (PCA) and Multivariate Curve Resolution (MCR) (PLS_Toolbox, Eigenvector Research, Inc., Manson, Wash.). This treatment, which is familiar to one skilled in the art, identified factors associated with variance in the spectral data. Factors 1, 2, 3, 4 and 5 showed different strengths, or "concentrations", for the colonies screened (FIG. 10). Specifically, Factor 1 described colonies of the *E. coli* GAL⁺ no reactant and *E. coli* GAL⁺+NPG types, Factor 2 described colonies of the *E. coli* GAL⁺+MUG type, Factor 3 described colonies of the *E. coli* GAL⁺+Bluo-Gal type, Factor 4 described colonies of the *E. coli* GAL⁺+S-Gal type, and Factor 5 described colonies of the *E. coli* GAL⁺+X-Gal type. The negative ToF-SIMS computed spectra associated with these five factors showed major spectral differences (FIG. 10). Therefore the TOF-SIMS data identified five characteristically different colony types. The description of both *E. coli* GAL⁺ and *E. coli* GAL⁺+NPG by Factor 1 is consistent with results from PCA alone described above that showed overlapping between *E. coli* GAL⁺+NPG and *E. coli* GAL⁺ no reactant.

Detection of the product negative molecular secondary ions provided the basis for the differentiation of *E. coli* expressing β-galactosidase with reactants Bluo-Gal, S-Gal and X-Gal. Specifically, Factor 3 showed a prominent feature at around m/z 420, which is consistent with the molecular weight of the dimer of cleaved product from Bluo-GAL. Factor 4 showed a prominent feature at m/z 231, which is consistent with the molecular weight of the cleaved product of S-GAL. Factor 5 showed a prominent feature at m/z 486, which is consistent with the molecular weight of the dimmer of cleaved product of X-GAL.

The spectral pattern for the *E. coli* GAL⁺+MUG colony type was differentiated easily from the other colony types, but the spectral pattern did not show a molecular ion for MU. The TOF-SIMS data provided a specific spectral pattern that was associated with MU production. This is similar to the case with cinnamic acid production that was discussed in Example 3.

Thus it was shown that, through detection of product-specific secondary ions or through the recognition of specific spectral patterns, TOF-SIMS was able to screen a range of *E. coli*-synthesized products.

Example 5

TOF-SIMS Detection of *Yarrowia lipolytica* Colonies Producing Different Fatty Acid Profiles in an Array This example involves a *Yarrowia lipolytica* strain engineered to produce a fatty acid profile which is different from that of wild type *Yarrowia*, which normally requires extensive sample preparation and sequential analysis by gas chromatography to differentiate. The TOF-SIMS method is able to differentiate between this strain and the wild type based on detection of fatty acid compositional differences. This example also demonstrates the preparation and analysis of colony replicas, a technique that can be used to screen collections of organisms by ToF-SIMS for use in screening a mutant collection.

Yeast Strains:

The strains of the yeast, *Yarrowia lipolytica*, that were used in this example had different fatty acid compositions and each was a nutritional auxotroph allowing selection. The wild type strain, called Q, was acquired from the ATCC with Accession number 76982. It primarily accumulates oleic (C18:1) and linoleic (C18:2) acids and is a leucine auxotroph (phenotype: leu⁻). The Q+4 strain was derived from Q by transformation with four genes to convert linoleic acid to eicosapentenoic acid (Delta 6 desaturase, elongase, delta 5 desaturase, delta 17 desaturase). It accumulates 10-15% gamma linolenic acid (C18:3) in addition to oleic and linoleic acids and is a uracil auxotroph (phenotype ura⁻).

Q+4 Strain Description:

The Q+4 strain is wild type *Yarrowia lipolytica*, ATCC #76982 that was transformed with a pGEM-T easy vector (Promega, Madison, Wis.) that contained a 10.3 kb DNA fragment (SEQ ID NO: 1) comprising the following sequences:

1) 440 bp of 5'-non-coding DNA sequence upstream from the *Yarrowia lipolytica* URA3 gene
2) a chimeric gene including a 418 bp TEF promoter (from a translation elongation factor gene) from the *Yarrowia lipolytica* genome (Muller S., et al. Yeast, 14: 1267-1283 (1998)), a 973 bp sequence containing the coding region of a *Mortierella alpina* (Accession #AF465281) high affinity PUFA elongase gene, and a 179 bp XPR2 transcriptional terminator (from the extracellular protease gene).
3) A chimeric gene including the TEF promoter above, a 1357 bp sequence containing the coding region of an *M. alpina* Δ5 desaturase gene, and the XPR2 transcription terminator.
4) A 2.25 kb sequence including the *Yarrowia* LEU2 gene
5) A chimeric gene including the TEF promoter, the *Saprolegnia diclina* (ATCC #56851) Δ17 desaturase coding region which had been codon optimized for expression in *Yarrowia*, and the XPR2 transcription terminator.
6) A chimeric gene including the TEF promoter, the *M. alpina* Δ6 desaturase coding region, and the XPR2 transcription terminator.
7) 280 bp of 3'-sequence from the *Yarrowia lipolytica* URA3 gene.

Preparation of Colony Plates/Growth:

Cultures of Q and Q+4 were grown on minimal media prepared as follows:

*Yarrowia* Minimal Medium (MM):
20 g/L glucose
1.7 g/L yeast nitrogen base without amino acids or ammonium sulfate
1 g/L proline
0.1 g/L lysine
0.1 g/L adenine The pH was adjusted to 6.1. For solid media, 1.5% agar was added. For growth of the Q leucine auxotroph, 0.1 g/L leucine was added (MML); for growth of the Q+4 uracil auxotroph, 0.1 g/L uracil and 0.1 g/L uridine were added (MMU). A combined medium permitting growth of both *Yarrowia* strains contained leucine, uracil and uridine at the same concentrations (MMUL).

Glycerol stocks were used to prepare a mixed culture of Q, Q+4, and an additional strain. The mixed culture was plated out on MMUL medium, and grown for 2 days at 30° C. The 10 cm diameter plate with approximately 1000 colonies was then replicated by laying a circle of sterile Supor® 200 polyethersulfone membrane on top of the culture dish, until the membrane was completely wetted (observed as uniform darkening of the filter). This membrane was then removed from the dish, flipped over so that the side in contact with the colonies was on top, and then placed on a new dish of MMUL medium. After incubation overnight at 30° C., the membrane had a pattern of colonies that was an exact replica of those on the original culture plate. An additional replicate membrane was made by repeating this process. Two marker dots were made with a Sanford Sharpie Fine Point Blue permanent marker in a line pointing to a notch that was cut out of both the original and the replica membranes. This notch corresponded to the location of a line on the edge of the original plate of medium, and aided in later alignment of the membranes, growth plate and the TOF-SIMS data. This notch was termed the radial registration mark.

Introduction of Colonies into the Vacuum Chamber for TOF-SIMS Analysis:

One entire Supor® polyethersulfone replica membrane was peeled off of the growth medium and mounted on a stainless steel circular holder by securing a stainless steel ring overlapping the edge of the membrane to the holder. The sample was then introduced into an Ion-ToF Model IV TOF-SIMS instrument (Ion-ToF, GmbH, Muenster, Germany) per the manufacturer's instructions. Pump-down from atmosphere to $<5\times10^{-6}$ torr was accomplished in a pre-chamber, after which the sample stage was pushed through to the main analysis chamber using a magnetic transfer rod, where the pressure was $<5\times10^{-7}$ torr.

Using the TOF-SIMS Image Data to Screen Colonies:

Colony screening was accomplished by using a gold primary ion source, a pulsed electron flood gun for charge compensation, and a spectrometer of the ion reflector type (Ion-ToF Model IV, Ion-ToF, GmbH, Muenster, Germany). The protocol for screening was as described in Example 2, "Colony Screening via TOF-SIMS Secondary Ion Mapping via Stage Rastering under the Primary Ion Beam". The sample stage was rastered over a 20×20 mm² area, with 256×256 pixel resolution. An entire negative secondary ion mass spectrum from 0-800 m/z was acquired at each approximately 78×78 μm² area pixel. Intensities of specific peaks from the mass spectral data at each pixel were then used to create a spatial distribution map.

The intensities of phosphate-related peaks at nominal m/z 63 (PO2−) and 79 (PO3−) for each pixel were summed and used to map the locations of all colonies within the area assayed (FIG. 10A), since phosphate functionality is associated with the cell membrane. A map of peak intensities corresponding to the marker dots was overlaid with the phosphate map in a different color and allowed easy registry with the original colony plate. Spectral data can be extracted from single or multiple pixels making up individual colonies. The negative TOF-SIMS spectral data was extracted from sets of pixels making up different colonies observed in the phosphate map from FIG. 11A. Three different spectral patterns were observed in the fatty acid region of the data for assayed colonies (FIG. 11A-C), two of which described the colonies of the Q and Q+4 strains (FIG. 11D). Referring to FIGS. 11A-D the letters in the top panel indicate colonies from which spectra are shown in FIG. 11D, and the numbers in the lower panels indicate colonies that were picked for confirmation of identification. Note that the colony labeled A is the same as that labeled 1 in the middle panel, and the colony labeled B is the same as that labeled 16 in the lower panel.

The third pattern described the other strain in the mixture, that is not presented herein. One spectral pattern had peaks at nominal m/z 279 and 281, consistent with production of linoleic (C18:2) and oleic (C18:1) fatty acids, respectively, which identified the colony as being the Q strain. The second pattern showed a marked increase in mm/z 281 intensity relative to m/z 279 intensity, and also showed a peak at nominal m/z 277, indicating production of gamma linolenic acid (C18:3), which identified the colony as being the Q+4 strain.

Based on the spectral differences, maps of secondary ion intensities per pixel were generated to indicate those colonies belonging to the Q, Q+4, and third strains. Specifically, a grayscale map of phosphate intensity/pixel was made to show locations of all colonies; a color overlay (blue) map of m/z 279 intensity/pixel, ratioed to m/z 281 intensity/pixel, was made to show locations of Q colonies; a color overlay (green) map of m/z 281 intensity/pixel, ratioed to m/z 279 intensity/pixel, was made to show locations of Q+4 colonies, and the third spectral pattern was also overlaid (red). These maps allowed identification of Q and Q+4 colonies based on color mapping of the colony array.

A Principal Components Analysis was carried out as described previously on normalized, mean-centered data for this dataset. The map locations and spectra of Principal Component 1 and Principal Component 2 are shown in the upper and lower panels of FIG. 12, respectively. This data distinguished different types of Yarrowia colonies.

Identity Verification of Colonies by Nutritional Screening/Culturing on Specific Media:

In order to track the colony identification made above back to the original master plate of colonies on an agar surface, an image of FIG. 11A was reduced in size to a 2 cm square (the actual size of the replica filter analyzed), and printed as a transparency. The transparency image was placed face down under the original master plate of colonies (surface side up) on a light box, and the image of colonies viewed through the transparency was visually aligned with the colonies on the plate. The proper orientation was important for correct alignment, as the colony replica that was scanned by TOF-SIMS was a mirror image of the original master plate. The (mirror) image of the scan was then aligned with the radial registration mark on the plate using the marker dots that point towards this mark, and moved until the pattern of colonies exactly corresponded to the image.

Once the pattern was matched with the actual colonies, this guide was used to pick representative colonies from the master plate for subsequent confirmation of their identity. Based on the false color overlay of the differing spectra described above, colonies that appeared predominantly blue were identified as Q, and numbers 1-12 in FIG. 11A were picked for testing. Similarly picked for testing were predominantly green colonies, numbered 13-18 in FIG. 11A, and identified as Q+4. The strategy for subsequent confirmation of the picked colonies utilized the different nutritional requirements of the strains. The Q strain requires leucine for growth and Q+4 requires uracil. Therefore Q grows only on MMUL, and not MMU or MM. Q+4 grows on MMU but not MM. The picked colonies were tested by inoculating onto media that permit growth based on the identification, and resulting cells were used to inoculate onto more restrictive media.

1. Colonies 1-12 were inoculated onto solid MMUL medium. All of these grew. Resulting cells were then inoculated onto MMU and MM media. Ten of the 12 colonies did not grow on either MMU or MM, confirming their identity as Q. Colony 6 grew on both MMU and MM, suggesting that it was not Q. Colony 11 grew a small number of discrete colonies on MM and MMU, suggesting that it was slightly contaminated, but most likely was Q. The ToF-SIMS mapping therefore correctly identified colonies of the Q strain in 11 out of 12 instances.

2. Colonies 13-18 were inoculated onto solid MMU medium. All of these grew. Resulting cells were then inoculated onto MM medium. Four of the six colonies did not grow on MM, confirming their identity as Q+4. Colony 14 grew on MM, suggesting that it was not Q+4. Colony 15 grew a small number of discrete colonies on MM, suggesting that it was slightly contaminated, but most likely was Q+4. The TOF-SIMS mapping therefore correctly identified colonies of the Q+4 strain in 5 out of 6 instances.

Example 6

TOF-SIMS Detection of Yarrowia lipolytica Colonies after Saponification on Supor® Filter This example demonstrates the processing of colonies on a filter by a treatment that enhances the ability to measure TOF-SIMS detectable product. The process used to alter the colonies and their products was a KOH base-catalyzed hydrolysis (saponification) of the constituent lipids. When performed in solution, this treatment yields free fatty acid salts.

Preparation of Saponified Colonies:

Only the Q+4 strain of the yeast, Yarrowia lipolytica, was used in this example. Two solid media plates of MMU media with sterile Supor® 200 polyethersulfone membranes on top were inoculated from a glycerol stock of Q+4 and grown for 48 hrs at 30° C.

For the saponification procedure, one of the Supor® filters with ~500 Yarrowia colonies was removed from the media, and allowed to air-dry for 2 minutes before being placed on a filter paper blotter (2 layers of Whatman No. 1, 9 cm diameter) saturated with a solution of 90% methanol, 10% water, and 0.3 M KOH. The filter paper had been previously cleaned by rinsing in methanol and air drying. The Supor® filter was left on this blotter for no more than 1 min, and then transferred to a hybridization tube (Corning, 35 mm×100 mm). The Supor® filter adhered to the walls of the tube. The tube was tightly sealed and completely immersed in a water bath at 80° C. After 1 hr in the water bath, the tube was removed, opened, and the filter allowed to air dry before removal from the tube. The colonies had lost most of their vertical definition and appeared as shiny yellow spots.

Introduction of Colonies into the Vacuum Chamber for TOF-SIMS Analysis:

For the treated array, and also the untreated array, a 1 $cm^2$ section of the Supor® polyethersulfone membrane was cut out, peeled off of the growth media, and back-mounted against a molybdenum mask forming part of a stainless steel multiple-sample holder. The sample was then introduced into an Ion-ToF Model IV TOF-SIMS instrument (Ion-ToF, GmbH, Muenster, Germany) per the manufacturer's instructions, as described previously.

Enhancement of TOF-SIMS Negative Secondary Ion Signal from Q+4 Yarrowia Colonies as a Result of the Saponification Procedure:

Colonies were each analyzed by using the following TOF-SIMS conditions: a Gold primary ion source, a pulsed electron flood gun for charge compensation, and a spectrometer of the ion reflector type. The colony area sampled was 250× 250 $\mu m^2$ for the unsaponified sample and 300×300 $\mu m^2$ for the saponified sample. This difference in analysis area was a consequence of the different colony sizes.

The enhancement of negative secondary ion signal in the fatty acid region was measured as follows: The area from m/z 250-290, which includes C16 and C18 fatty acids, was ratioed to the total negative ion yield. An increase in this ratio of 1.7 was observed for the spectrum from the saponified sample, when compared to the untreated sample (FIG. 13).

In another experiment, an air dried Supor® filter with *Yarrowia* colonies was placed on a filter paper blotter (2 layers of Whatman No. 1, 9 cm diameter) that was saturated with a solution 0.3 M KOH in water, with no methanol included. The filter was incubated and assayed as described above. This treatment with KOH alone gave an enhancement of the signal-to-noise ratio similar to that obtained using KOH with methanol. Eliminating methanol may be beneficial as it lowers the possibility that dissolved fatty acids may diffuse away from their point of origin in the colony during the treatment.

Example 7 (Prophetic)

Identification of Specific Microorganisms by TOF-SIMS Analysis of Fatty Acid Composition This example demonstrates the identification of specific microorganisms with distinctive fatty acid profiles based on TOF-SIMS analysis determination of the fatty acid profile for the organims.

Background:

Fatty acid analysis has been used in the characterization of numerous bacteria and fungi [see for example Komagata, K. & Suzuki, K. (1987). Lipid and cell-wall analysis in bacterial systematics. *Methods in Microbiology*, 19:161-207.); Stead, D. E., Sellwood, J. E., Wilson, J. & Viney, I. (1992). Evaluation of a commercial microbial identification system based on fatty acid profiles for rapid, accurate identification of plant pathogenic bacteria. *Journal of Applied Biochemistry*, 72: 315-321.); and Welch, D. F. (1991). Applications of cellular fatty acid analysis. *Clinical Microbiology Reviews*, 4: 422-438.).

In some cases a specific microorganism has a very characteristic fatty acid profile that is diagnostic for the presence of that organism or for the response of the organism to specific environmental conditions. For example the Gilardi rod group 1 bacteria that are commonly found in human wounds have a distinctive fatty acid profile (Moss et al, Journal of Clinical Microbiology (1993) 31: 689-691). The food pathogen *Listeria monocytogenes* has an unusually high composition of certain branched chain fatty acids (Moss et al, Journal of Clinical Microbiology (1993) 31: 689-691). The extraction of fatty acids and analysis by traditional techniques like gas chromatography of the fatty acid methyl esters is tedious and time consuming, especially if it has to be done on many samples. Using the procedures outlined here, a much more rapid screen of the fatty acids of microorganisms is possible, A sample of microorganisms is collected by standard methods and grown into colonies on a Supor® polyethersulfone membrane filter. A replica of the colony array is made as decribed in Example 5, adding a radial registration mark and marker dots. A colony-arrayed filter is placed in the TOF-SIMS instrument and assayed as described in Example 5. A Principal Components Analysis is carried out as described previously on normalized, mean-centered data. This analysis is used to identify fatty acid compositions of the microorganisms in the colonies on the filter. Based on the fatty acid compositions of individual colonies, the presence of a specific microorganism is ascertained.

What is claimed is:

1. A method for identifying a biological organism making a ToF-SIMS detectable product comprising:
   a) providing a colony comprised of biological organisms, on a vacuum compatible support, wherein the biological organisms of the colony produce a product detectable by ToF-SIMS;
   b) performing ToF-SIMS analysis on the colony of (a) to produce data; and
   c) correlating the data of (b) with the colony of (a) whereby biological organism making a ToF-SIMS detectable product is identified.

2. A method for identifying a biological organism making a ToF-SIMS detectable product comprising:
   a) providing a mixed population of biological organisms presented in a two dimensional array on a vacuum compatible support wherein at least one of the organisms produces a product detectable by ToF-SIMS;
   b) performing ToF-SIMS analysis on the array of organisms of (a) to produce data;
   c) mapping said array wherein each organism is supplied with a unique locus on the array;
   d) identifying at least one locus on the array where a ToF-SIMS detectable product is present; and
   e) correlating said data with the unique organism locus of (c) whereby the organism producing a ToF-SIMS detectable product is identified.

3. A method for identifying a biological organism making a ToF-SIMS detectable product comprising:
   a) providing a mixed population of biological organisms presented in a two dimensional array on a vacuum compatible support wherein at least one of the organisms produces a primary product;
   (b) contacting the array of (a) with a substance under conditions whereby the primary product reacts to produce a ToF-SIMS detectable product;
   c) performing ToF-SIMS analysis on the array of organisms of (a) to produce data;
   d) mapping said array wherein each organism is supplied with a unique locus on the array;
   e) identifying at least one locus on the array where a ToF-SIMS detectable product is present; and
   f) correlating said data with the unique organism locus of (d) whereby the organism producing a ToF-SIMS detectable product is identified.

4. A method for identifying a biological organism making a ToF-SIMS detectable product comprising:
   a) providing a mixed population of biological organisms presented in a two dimensional array on a vacuum compatible support;
   b) transferring the array to a secondary growth medium wherein at least one of the biological organisms incubated on the secondary growth medium produces a product detectable by ToF-SIMS;
   c) performing ToF-SIMS analysis on the array of organisms of (a) to produce ToF-SIMS data;
   d) mapping said array wherein each organism is supplied with a unique locus on the array;
   e) identifying at least one locus on the array where a ToF-SIMS detectable product is present; and
   f) correlating said data with the unique organism locus of (d) whereby the organism producing a ToF-SIMS detectable product is identified.

5. A method according to any of claim 2, 3 or 4 wherein said mapping of said array is performed with ToF-SIMS data.

6. A method according to any of claim 2, 3 or 4 wherein said identifying at least one locus on the array is performed with ToF-SIMS data.

7. A method according to any of claim 2, 3, or 4 wherein the mixed population of organisms is grown on a primary medium in a two dimensional array prior to placement on a vacuum compatible support.

8. A method according to any of claim 1,2,3 or 4 wherein the biological organism is selected from the group consisting of prokaryotes and eukaryotes.

9. A method according to claim 8 wherein the biological organism is a plant cell.

10. A method according to claim 9 wherein the biological organism is selected from the group consisting of maize, rice, wheat, soybean, tobacco, and arabidopsis.

11. A method according to claim 8 wherein the biological organism is selected from the group consisting of a yeast and a bacterium.

12. A method according to claim 11 wherein the biological organism is selected from the group consisting of *Saccharomyces, Pichia, Yarrowia, Rhodococcus, Streptomyces, Actinomycetes, Corynebacterium, Bacillus, Escherichia, Pseudomonas, Salmonella, Erwinia, Penicillium, Fusarium, Aspergillus, Podospora, Chrysosporium, Trichoderma*, and *Neurospora*.

13. A method according to any of claims 1, 2, 3 and 4 wherein the organism forms colonies.

14. A method according to any of claims 1, 2, 3 and 4 wherein the vacuum compatible substrate is selected from the group consisting of: nylon, nitrocellulose, polyethersulfones, polysulfones, polycarbonate, polystyrene, silicon/silica, and glassy carbon.

15. A method according to any of claims 1, 2, 3 and 4 wherein the ToF-SIMS detectable product is selected from the group consisting of: fatty acids, p-hydroxycinnamic acid, cinnamic acid, beta-galactosidase products.

16. A method according to claim 15 wherein the fatty acid is selected from the group consisting of: lauric acid, myristic acid, palmitic acid, stearic acid, oleic acid, linoleic acid, linolenic acid, di-homo-gamma linoleic acid, arachidonic acid, stearidonic acid, eicosatetraeneoic acid, eicosapentaenoic acid, docosahexaenoic acid, hydroxy fatty acids, peroxy fatty acids, branched chain fatty acids, phospholipids and phospholipid fragments, triglycerides and triglyceride fragments.

17. A method according to claim 3 wherein the primary product is released to react with the reactant by the process of saponification.

18. A method according to claim 17 wherein the saponification is accomplished in the presence of potassium hydroxide and in the absence of methanol.

19. A method according to any of claim 2, 3 or 4 wherein the unique organism locus is supplied by generating an optical picture of the array to assign a unique locus to each organism on the array.

20. A method according to any of claim 1, 2 or 4 wherein the ToF-SIMS product is equal to or less than 8 kD.

21. A method according to any of claim 2, 3, or 4, wherein ToF-SIMS analysis collects data at each pixel of a two-dimensional pixel array spanning the dimensions of the array.

22. A method according to any of claim 1, 2, 3, or 4, wherein the ToF-SIMS data is refined via chemometric methods.

23. A method according to claim 22 wherein the chemometric methods are selected from the group consisting of Principal Components Analysis (PCA) and Multivariate Curve Resolution (MCR).

* * * * *